United States Patent
Davis et al.

(10) Patent No.: US 7,098,183 B2
(45) Date of Patent: Aug. 29, 2006

(54) **NUCLEOTIDE AND AMINO ACID SEQUENCES OF OOCYTE FACTORS FOR ALTERING OVARIAN FOLLICULAR GROWTH *IN VIVO* OR *IN VITRO***

(76) Inventors: George Henry Davis, School Road, 2RD, Mosgiel (NZ); Susan May Galloway, 197 Balmacewen Rd, Dunedin (NZ); Kenneth Pattrick McNatty, P.O. Box 40479, Upper Hutt (NZ); Olli Visa-Pekka Ritvos, Oxelvâgen 4, 19732, Bro (SE); Jennifer Lee Juengel, 45 Sunnyview Dr, Upper Hutt (NZ); Kaisa Niina Johanna Vuojolainen, Koskelantie 23 H 67, 00610, Helsinki (FI); Mika Petri Esaias Laitinen, Peltovuorenkuja 7, 01690, Vantaa (FI)

( * ) Notice: Subject to any disclaimer, the term of this patent is extended or adjusted under 35 U.S.C. 154(b) by 0 days.

(21) Appl. No.: 10/311,664

(22) PCT Filed: Jun. 15, 2001

(86) PCT No.: PCT/NZ01/00113

§ 371 (c)(1), (2), (4) Date: Jul. 19, 2004

(87) PCT Pub. No.: WO01/96393

PCT Pub. Date: Dec. 20, 2001

(65) Prior Publication Data

US 2004/0267003 A1   Dec. 30, 2004

(51) Int. Cl.
*A61K 38/18* (2006.01)
*C07K 14/475* (2006.01)
*C07K 14/495* (2006.01)
*C07K 14/51* (2006.01)
*G01N 33/53* (2006.01)

(52) U.S. Cl. .......... 514/2; 514/8; 514/12; 530/350; 530/397; 530/399; 435/7.21

(58) Field of Classification Search ............. 530/350, 530/397; 514/2
See application file for complete search history.

(56) References Cited

U.S. PATENT DOCUMENTS 6,790,824 B1 * 9/2004 Unsicker et al. ............. 514/2
6,872,698 B1 * 3/2005 Marchionni et al. ......... 514/2

FOREIGN PATENT DOCUMENTS

WO    WO 00/32222    *   6/2000

OTHER PUBLICATIONS

Stratagene 1991 Product Catalog. Prime-It Random Primer Labeling Kit, Cat. #300387.*
Jaatinen et al. (1999), Mol. Cell. Endocrin. 156: 189-193.*
Hsueh et al., Mol Cell Endocrinol. May 25, 2000; 163: 95-100.*
Dube, J.L., 1998, "The bone morphogenetic protein 15 gene is X-linked and expressed in oocytes", *Molecular Endocrinology*, 12:1809-1817.

* cited by examiner

*Primary Examiner*—Elizabeth Kemmerer
*Assistant Examiner*—Christina Borgeest
(74) *Attorney, Agent, or Firm*—Knobbe Martens Olson & Bear, LLP

(57) ABSTRACT

Aspects of the present invention relate to nucleotide and amino acid sequences of oocyte factors for altering ovarian follicular growth in vivo or in vitro. The present invention also concerns novel homodimeric and heterodimeric polypeptides and their use for altering mammalian ovarian follicular growth in vivo or in vitro.

13 Claims, 2 Drawing Sheets

Figure 1

```
-27                                              1
ATG TTG CTG AAC ACC AAG CTT TTC AAG ATG GTC CTC CTG AGC
 M   L   L   N   T   K   L   F   K   M   V   L   L   S

ATC CTT AGA ATC CTT CTT TGG GGA CTG GTG ....
 I   L   R   I   L   L   W   G   V   L
```

NUCLEOTIDE AND AMINO ACID SEQUENCES OF OOCYTE FACTORS FOR ALTERING OVARIAN FOLLICULAR GROWTH IN VIVO OR IN VITRO

CROSS-REFERENCE TO RELATED APPLICATIONS

This is the U.S. National Phase under 35 U.S.C. § 371 of International Application No. PCT/NZ01/00113, filed Jun. 15, 2001, designating the United States and published in English, which claims priority to New Zealand Application No. 502796, filed Jun. 15, 2000.

FIELD OF THE INVENTION

The present invention relates to nucleotide and amino acid sequences of oocyte factors for altering ovarian follicular growth in vivo or in vitro. The present invention also concerns novel homodimeric and heterodimeric polypeptides and their use for altering mammalian ovarian follicular growth in vivo or in vitro. In particular, the invention broadly concerns active or passive immunisation against these homo- or heterodimeric polypeptides or functional fragments or variants thereof so as to alter follicular growth in vivo or in vitro.

BACKGROUND OF THE INVENTION

The molecular nature of regulatory molecules responsible for stimulating early phases of ovarian folliculogenesis (i.e. the growth and differentiation of primordial follicles to primary, secondary, and pre-antral follicles) has been poorly understood. On the other hand, follicle-stimulating hormone (FSH) and luteinising hormone are glycoprotein hormones derived from the pituitary and have generally been accepted as the key factors regulating the later stages of ovarian folliculogenesis.

Moreover FSH is accepted as the single most important factor for stimulating a greater than normal number of follicles to ovulate, a fact that is well illustrated by the wide use of commercial FSH preparations in ovarian hyperstimulation regimes both in medicine and veterinary medicine. Recent studies have indicated that early folliculogenesis is controlled by intraovarian factors of which the granulosa cell-derived stem cell factor (or c-kit ligand) and the oocyte-derived growth differentiation factor-9 (GDF-9) have gained most attention, because both appear to be essential for early mammalian folliculogenesis.

GDF-9 was first described in 1993 as a novel member of the transforming growth factor beta (TGF-β) superfamily which is specifically expressed in the ovary (McPherron and Lee, 1993). Like other members of the TGF-β family, GDF-9 is encoded as a prepropeptide consisting of a signal peptide, a proregion, and a so called C-terminal mature region, which is cleaved from the precursor peptide by an intracellular protease belonging to a group of furin-like proteases. Growth factors of the TGF-β family are characterised by a common pattern of cysteine residues found in the mature region that is likely to form in all members of the family; this is a rigid intramolecular structure known as the "cysteine knot" which is composed of six Cys residues forming three characteristic disulphide bridges in a monomer of a TGF-β family member (Daopin et al., 1992; Schlunegger and Grutter, 1992 and 1993; Griffith et al., 1996; Scheufler et al., 1999). Most members of the TGF-β family have a conserved seventh Cys residue that is responsible for the covalent homodimerisation of two identical monomers (homodimers) or for the heterodimerisation of a given TGF-β family member with another distinct member of the family (heterodimers).

In mice, GDF-9 is expressed in oocytes from the primary stage of follicular development until ovulation (McGrath et al., 1995; Laitinen et al., 1998). Using the mouse GDF-9 sequence as a test sequence for the data base searches we identified, a GDF-9 like expressed sequence tag (EST) cDNA derived from a 2-cell mouse embryo library (Laitinen et al., 1998). We showed that the transcript of this novel factor, GDF-9B, which is 55% homologous to GDF-9, is expressed in oocytes of the mouse ovary at the same time as GDF-9 (Laitinen et al., 1998). Using PCR and primers derived from the mouse EST sequence we amplified a fragment of the corresponding gene from human genomic DNA, mapped the gene locus to chromosome Xp11.2, and deduced the human GDF-9B gene structure from isolated cosmid clones (Aaltonen et al., 1999). Interestingly, in the human ovary, GDF-9 mRNA expression begins in primary follicles slightly earlier than that of GDF-9B (Aaltonen et al., 1999). The mouse and human GDF-9B genes have been cloned and the protein encoded by the gene has also been named bone morphogenetic protein 15 (BMP-15) (Dube et al., 1998).

GDF-9 appears to be essential for ovarian folliculogenesis. From the literature it is known that GDF-9 deficient mice (GDF-9-/-) are infertile due to an early arrest in folliculogenesis (Dong et al., 1996). In GDF-9-/- ovaries folliculogenesis stops at the primary follicle stage when one layer of cuboidal granulosa cells surrounds the oocyte. Even though the oocyte continues to grow, the granulosa cells fail to proliferate and no thecal cell differentiation is associated with follicular enlargement.

The Inverdale fecundity gene (FecX[1]) was identified as a major gene affecting the prolificacy of a Romney flock of sheep (Davis et al., 1991). Segregation analyses determined that the gene is carried on the X-chromosome, and that ewes carrying a single copy of the gene (I/+) have litter size about 0.6 lambs larger than noncarrier ewes (+/+). The increase in number of lambs born is directly linked to an altered pattern of follicular development and an increase in ovulation-rate above that in the 2 wild-type of ~1.0 (Shackell et al., 1993; Davis et al., 1991). By contrast, homozygous carrier ewes having two copies of the gene (I/I) are infertile; due to an ovarian failure condition (Davis et al., 1992). In ovaries of the (I/I) ewe, folliculogenesis stops at the primary follicular stage and the phenotype is not dissimilar to that seen in GDF-9 (-/-) mice (Braw-Tal et al., 1993; McNatty et al., 1995; Smith et al., 1997).

A second prolific Romney flock (Hanna, 1995) with no known connection to the Inverdale flock was also shown to carry an X-linked mutation with similar phenotype to Inverdale. Evidence that the Hanna animals carried a mutation (FecX[H]) in the same gene as for Inverdale was obtained when infertile females were produced by mating Inverdale carrier rams with carrier Hanna ewes (Davis et al., 1995). The Hanna line has been maintained at the Invermay AgResearch Centre as a distinct group alongside the Inverdale line.

In New Zealand Patent Application No. 500844 we, the present inventors, identified in Inverdale sheep a nucleotide substitution beyond the mature peptide processing site of the GDF-913 gene which converts the codon GTC (amino acid valine (V) to GAC (amino acid aspartic acid (D)). We also showed that in Hanna sheep the C nucleotide beyond the mature peptide processing site is converted to a T. This converts a codon CAG (coding for glutamine (Q)) to a codon TAG (coding for termination) thereby resulting in a truncated mature protein. These respective mutations in Inverdale and Hanna are suggested to be the underlying causes for the "streak" ovaries and anovulatory conditions in homozygous Inverdale or Hanna ewes and in the Inverdale cross Hanna ewes.

Previously it has been shown that GDF-9-/- mice are infertile showing that GDF-9 is important for normal fertility in some mammals. However, with the discovery of the related oocyte-specific factor GDF-9B several novel findings were found by us to support the notion that: (1) GDF-9B is essential for normal folliculogenesis in some mammals; (2) that GDF-9B is critically important for determining the ovulation rate in some mammals and; (3) since GDF-9 and GDF-9B are coexpressed by oocytes, they function co-operatively to enhance both follicular development and ovulation rate. Collectively these novel hypotheses were only made possible by our discovery of the Inverdale and Hanna GDF-9B mutations in sheep.

The inventors have for the first time determined the full gene structure of the sheep GDF-9B gene encoding the wild-type protein and have shown that it is necessary for maintaining normal ovarian folliculogenesis in sheep. The inventors have also identified the full gene structure of the GDF-9B variants in Inverdale and Hanna sheep which cause higher than normal ovulation rates in heterozygous animals and infertility in homozygous animals. It is broadly to the full-length wildtype and mutated GDF-9B sequences and variants thereof and their use in the modulation of mammalian fertility that the present invention is directed.

All references, including any patents or patent applications, cited in this specification are hereby incorporated by reference. No admission is made that any reference constitutes prior art. The discussion of the references states what their authors assert, and the applicants reserve the right to challenge the accuracy and pertinency of the cited documents. It will be clearly understood that, although a number of prior art publications are referred to herein, this reference does not constitute an admission that any of these documents forms part of the common general knowledge in the art, in New Zealand or in any other country.

SUMMARY OF THE INVENTION

Accordingly, to a first aspect, the present invention provides an isolated wildtype GDF-9B nucleic acid molecule comprising a nucleotide sequence selected from the group consisting of:

a) SEQ ID NO: 1;
b) a sequence able to hybridise under stringent conditions to the molecule in (a);
c) a sequence which is a functional variant or fragment of the molecule in (a);
d) a sequence complementary to the molecule defined in (a), (b) or (c); and
e) an anti-sense sequence corresponding to any of the molecules in (a)–(d).

In a second aspect, the present invention provides an isolated full length mutated GDF-9B nucleic acid molecule comprising a nucleotide sequence selected from the group consisting of:

a) SEQ ID NO: 3 or SEQ ID NO: 5;
b) a sequence able to hybridise under stringent conditions to the molecule(s) in (a);
c) a sequence which is a functional variant or fragment of the molecule(s) in (a);
d) a sequence complementary to the molecule(s) defined in (a), (b) or (c); and
e) an anti-sense sequence corresponding to any of the molecule(s) in (a)–(d).

The nucleic acid molecule may be an RNA, cRNA, genomic DNA or cDNA molecule, and may be single- or double-stranded. The nucleic acid molecule may also optionally comprise one or more synthetic, non-natural or altered nucleotide bases, or combinations thereof.

In a third aspect, the present invention provides an isolated full-length GDF-9B polypeptide comprising an amino acid sequence selected from the group consisting of:

a) SEQ ID NO: 2, SEQ ID NO: 4; or SEQ ID NO: 6; and
b) A functional variant or fragment of the sequence(s) in (a).

In a fourth aspect, the present invention provides a homodimeric mature GDF-9B polypeptide having subunits comprising an amino acid sequence selected from the group consisting of SEQ ID NO: 2 or a functional fragment or variant of said sequence.

In the fifth aspect, the present invention provides a heterodimeric polypeptide having subunits selected from the group consisting of:

a) A mature GDF-9B polypeptide comprising an amino acid sequence derived from SEQ ID NO: 2 or functional fragment or variant of said sequence; and
b) A mature GDF-9 polypeptide or a functional variants or fragments thereof.

The present invention further provides in a sixth aspect a method of expressing biologically active processed homodimeric GDF-9B polypeptide comprising the steps of:

a) generating an expression construct comprising a nucleic acid molecule comprising a nucleic acid sequence selected from the group consisting of SEQ ID NO: 1 or a functional fragment or variant of said sequence of the group;
b) transfecting a suitable cells with said construct;
c) selecting stable clones; and
d) isolating and purifying the expressed polypeptide.

In a seventh aspect, the present invention provides a method of expressing biologically-active processed heterodimeric GDF-9B and GDF-9 polypeptides comprising the steps of:

a) generating an expression construct containing a nucleic acid molecule comprising:

(i) a nucleic acid sequence selected from the group consisting of SEQ ID NO: 1 or a functional fragment or variant of said sequence; and (ii) a nucleic acid molecule encoding GDF-9 or a functional fragment or variant thereof;

b) transfecting suitable cells with said construct;

c) selecting stable clones; and isolating and purifying the expressed polypeptide.

Preferably the cells transfected are vertebrate, however the use of other cell types is envisaged.

The GDF-9 nucleic acid and protein sequences are available in public databases such as GenBank and SWISS-PROT. The accession number for the sheep GDF-9 nucleic acid is AF078545 and for protein is AAC28089.

Also provided by the present invention are recombinant expression vectors which contain a DNA molecule of the invention or functional variant thereof, and hosts transformed with a vector of the invention capable of expressing a polypeptide of the invention.

An additional aspect of the present invention provides a ligand which binds to a polypeptide of the invention. Most usually, the ligand is an antibody. It should be appreciated that the term "antibody" encompasses fragments or analogues of antibodies which retain the ability to bind to a polypeptide of the invention, including but not limited to Fv, $F(ab)_2$ fragments, ScFv molecules and the like. The antibody may be polyclonal or monoclonal, but is preferably monoclonal. In some embodiments the ligand may be a phage display molecule generated against polypeptides of the present invention, a single cell surface receptor or complex cell surface receptor. The polypeptide or peptide may be present as a monomer, dimer, heterodimer, multimer or a variant thereof.

In an eighth aspect, the invention provides a method for assessing the activity of GDF-9B homodimers and/or GDF-9B/GDF-9 heterodimers, comprising the steps of:

a) adding an effective amount of a GDF-9B homodimeric polypeptide; and/or a GDF9B/GDF-9 heterodimeric polypeptide to an ovarian cell or organ culture with or without other ovarian growth factors such as IGF-1 and/or other members of the transforming growth factor superfamily (e.g. activin, BMP2, TGFβ1); and b) conducting a bioassay on said cell or organ culture to assess the biological activity of said homodimeric and heterodimeric polypeptides.

In a ninth aspect, the invention provides transgenic animal models useful for demonstrating the effect of systemic production of GDF-9B homodimers and GDF-9B/GDF-9 heterodimers on follicular growth.

In a tenth aspect, the invention provides a method of adenoviral, retroviral and alphaviral transfer of GDF-9B expression cassettes or GDF-9 expression cassettes to host cells or organisms to thereby effect in vivo expression of GDF-9B homodimers or GDF-9B /GDF-9 heterodimers, comprising the step of transferring into a recipient cell, organ culture or recipient animal, a recombinant adenovirus including an expression cassette comprising a nucleic acid molecule having a nucleotide sequence selected from the group consisting of SEQ ID NO: 1 or a functional fragment or variant of said sequence, said nucleic acid molecule being in operative association with an expression control sequence.

In an eleventh aspect the present invention provides the use of an agent selected from the group consisting of:

a) a homodimeric polypeptide having subunits comprising GDF-9B or a functional fragment or variant thereof with or without homodimeric polypeptide having subunits comprising GDF-9 polypeptide or a functional fragment or variant thereof;

b) a heterodimeric polypeptide having subunits comprising GDF-9B and GDF-9 polypeptides, or functional fragments or variants of said GDF-9B or GDF-9 polypeptides;

together with or without supplementary gonadotrophins (e.g. FSH and/or LH) and/or other ovarian growth factors such as IGF-I, kit ligand (stem cell factor), epidermal growth factor or a member of the TGFβ superfamily (i.e. an agonist or antagonist) to:

1) alter follicular growth in ovaries of a mammal or other vertebrate either in vivo or in vitro; or 2) alter isolated ovarian cell growth/maturation in vitro (e.g. oocyte—cumulus cells and/or granulosa cells).

In yet a twelfth aspect, the invention provides a composition comprising an effective amount of an agent selected from the group consisting of:

a) a homodimeric polypeptide having subunits comprising a GDF-9B polypeptide or a functional fragment or variant thereof with or without homodimeric polypeptide having subunits comprising GDF-9 polypeptide or a functional fragment or variant thereof;

b) a heterodimeric polypeptide having subunits comprising a GDF-9B polypeptide and a GDF-9 polypeptide, or functional fragments or variants of said GDF-9B or GDF-9 polypeptides;

together with a pharmaceutically or veterinarily acceptable carrier (including adjuvants) or diluent; and optionally including supplementary gonadotrophins and/or other relevant ovarian growth factor agonists/antagonists.

In a thirteenth aspect the invention provides a method of altering ovarian follicular growth in a female mammal or other female vertebrate, in vivo said method comprising the step of transforming mammalian and other vertebrate ovarian host cells with GDF-9B and GDF-9 expression cassettes to allow over-expression of GDF-9B homodimers and GDF-9B/GDF-9 heterodimers.

In a fourteenth aspect the invention provides a method of altering ovarian follicular growth in a, female mammal or other female vertebrate, in vitro said method comprising the step of transforming mammalian and other vertebrate ovarian host cells with GDF-9B and GDF-9 expression cassettes to allow over-expression of GDF-9B homodimers and GDF-9B/GDF-9 heterodimers.

According to a further aspect the invention provides a nucleic acid molecule comprising a nucleotide sequence selected from the group consisting of SEQ ID NO: 11, SEQ ID NO: 13 and SEQ ID NO: 15, or a functional fragment of variant of said sequence.

According to a further aspect the invention provides a polypeptide comprising an amino acid sequence said from the group consisting of SEQ ID NO: 12 and SEQ ID NO: 16, or a functional fragment or variant of said sequence.

According to another aspect the invention provides a method of altering follicular growth comprising the step of introducing a ligand as claimed in any one of claims 9–15 to:

i) alter follicular growth in ovaries of a mammal or other vertebrate either in vivo or in vitro; or ii) alter isolated ovarian cell growth/maturation in vitro.

Preferably said mammal is selected from the group comprising sheep, cattle, goats, deer, pigs, humans, horses, camelids and possums, cats and dogs and any other commercially important species having a GDF-9B gene having a substantial identity to the GDF-9B sequences of the present invention. Said vertebrate is preferably selected from the group comprising chickens, ducks, geese, salmon and any other commercially important species having a substantial identity to the GDF-9B sequences of the present invention.

BRIEF DESCRIPTION OF THE DRAWINGS

In particular, preferred aspects of the invention will be described in relation to the accompanying drawings, in which:

FIG. 1. Shows the additional upstream ATG codon present in sheep genomic DNA. If this codon is used for protein translation initiation the translated protein is illustrated here. Genomic nucleotide sequence is on the upper line (SEQ ID NO: 9) and translated amino acid sequence on the lower lane (SEQ ID NO: 10). Numbers above the line indicate nucleotide numbers relating to SEQ ID NO: 1,. The position of the conserved initiation codon is underlined.

DETAILED DESCRIPTION OF THE INVENTION

Figure 2:
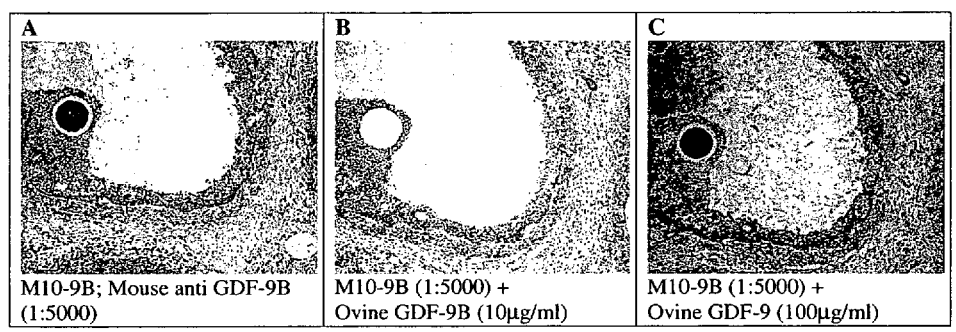
FIG. 2. Shows photomicrograph illustrating the localisation of GDF-9B in an oocyte. A. Dark staining indicates immunolocalisation of GDF-9B to an oocyte in a sheep ovary. B. Evidence that the staining shown in A can be prevented by preincubation of mouse GDF-9B antibody with an E. ccli derived mature ovine GDF-9B peptide. C. Evidence that the GDF-9B immunostaining of oocytes can not be removed by preincubation of mouse GDF-9B antibody with an excess of E. ccli derived mature ovine GDF-9 peptide.

As discussed above, the primary focus of the invention is the modulation of ovarian follicular growth via GDF-9B homodimers and GDF-9B/GDF-9 heterodimers activity in vivo and in vitro.

The term "isolated" means substantially separated or purified from contaminating sequences in the cell or organism in which the nucleic acid naturally occurs and includes nucleic acids purified by standard purification techniques as well as nucleic acids prepared by recombinant technology, including PCR technology, and those chemically synthesised.

Preferably, the nucleic acid molecule of SEQ ID NO: 1 is isolated from sheep genomic DNA, and that of SEQ ID NO: 3 and SEQ ID NO: 5 is isolated from DNA of sheep expressing the Inverdale or Hanna phenotype.

It has been noted that a polymorphism may occur in the signal peptide of GDF-9B in sheep (SEQ ID NO: 7, SEQ ID NO: 8). The predicted signal sequence appears to be around 25 amino acids long as predicted using the Signal P program (Signal P VI. 1 server at genome.cbs.dtu.dk/services/SignalP) (Neilsen et al., 1997) from ATG (Met) to ACA (Thr) in SEQ ID NO: 7 and SEQ ID NO: 8. A 3 base pair deletion is observed in some sheep where one of the two CTT sequences is not present. Therefore some sheep have a shorter signal sequence although most have the full length. From studies of Hanna, Hanna cross Inverdale, Inverdale and wild-type sheep either related or unrelated to Inverdale or Hanna, most were homozygous for two CTT's, although some were heterozygous for one CTT. The prevalence of the shorter version of the signal peptide was found to be high in the Merino breed of sheep but low in Romney breeds indicating that the polymorphism may be related to breed. Most Romney sheep carried the longer signal sequence regardless of their carrier status for Inverdale or Hanna. Although this polymorphism needs to be acknowledged it does not effect or modify the claims made in this invention.

It has also been noted that an additional, "in-frame" ATG start codon is present in the sheep genomic DNA sequence 27 nucleotides upstream from the GDF-9B ATG start codon (SEQ ID NO: 9, SEQ ID NO: 10). This sequence is present in all sheep sequenced, whether wildtype, Inverdale or Hanna carriers, and is clearly independent of the Inverdale and Hanna mutations. It is not known whether this upstream start codon is used during protein translation in sheep (SEQ ID NO: 9, SEQ ID NO: 10). If so it would result in a signal sequence of an additional 9 amino acids. Such a difference between sheep and other mammalian GDF-9B proteins would be unlikely to affect the function of the mature protein as this portion of the molecule is cleaved off in the active mature GDF-913, but we mention the possibility of an alternative protein translation start site which may be present in sheep. The signal peptide prediction program (Neilsen et al., 1997) indicates that this additional 9 amino acid sequence may function as a signal peptide and that the likely end site for the signal peptide would still be the Thr (T) amino acid indicated in SEQ ID NO: 7 and SEQ ID NO: 8.

In a further aspect, the present invention provides an isolated polypeptide selected from the amino acid sequences of SEQ ID NO: 2, SEQ ID NO: 4 and SEQ ID NO: 6 or a functional variant thereof which functions to manipulate ovarian follicular growth in a female mammal.

The polypeptide may be produced by expression of a suitable vector comprising the nucleic acid molecule of the invention or a functional variant thereof, in a suitable host cell as would be understood by a person skilled in the art.

The term "variant" as used herein refers to nucleotide and polypeptide sequences wherein the nucleotide or amino acid sequence exhibits substantially 50% or greater homology with the nucleotide or amino acid sequence of SEQ ID NOs: 1–6 respectively, preferably 75% homology and most preferably 90–95% homology to the sequences of the present invention: provided said variant has a biological activity as defined herein. The variant may be arrived at by modification of the native nucleotide or amino acid sequence by such modifications as insertion, substitution or deletion of one or more nucleotides or amino acids or it may be a naturally occurring variant. The term "variant" also includes homologous sequences which hybridise to the sequences of the invention under standard or preferably stringent hybridisation conditions familiar to those skilled in the art. Examples of the in situ hybridisation procedure typically used are described in (Tisdall et al., 1999); (Juengel et al., 2000).

Where such a variant is desired, the nucleotide sequence of the native DNA is altered appropriately. This alteration can be made through elective synthesis of the DNA or by modification of the native DNA by, for example, site-specific or cassette mutagenesis. Preferably, where portions of cDNA or genomic DNA require sequence modifications, site-specific primer directed mutagenesis is employed, using techniques standard in the art.

A "fragment" of a nucleic acid is a portion of the nucleic acid that is less than full length, and comprises at least a minimum sequence capable of hybridising specifically with a nucleic acid molecule according to the invention, or a sequence complementary thereto, under stringent conditions as defined below. A "fragment" of a polypeptide is a portion of the polypeptide which is less than full length, but which still retains the biological activity as defined herein.

The term "biologically active" refers to a polypeptide of the invention which is able to elicit a measurable physiological effect in the ovary or ovarian cell of a mammal or other vertebrate. The physiological effects may be measured by assays such as the incorporation of tritiated thymidine into granulosa cells. An example of such an assay is one in which follicles (1–2.5 mm diameter) are dissected free from ovarian stroma and granulosa cells isolated from theca and oocyte cumulus complexes. The cells are washed and resuspended in fresh media at a final concentration for bioassay of 100,000 viable cells per well and incubated with or without polypeptide for 48 hours.

At this time incorporation of tritiated thymidine is measured.

The term "protein (or polypeptide)" refers to a protein encoded by the nucleic acid molecule of the invention, including fragments, mutations and homologs having the same biological activity i.e. ovulation manipulation activity. The polypeptide of the invention can be isolated from a natural source, produced by the expression of a recombinant nucleic acid molecule, or can be chemically synthesised.

The term "ligand" refers to any molecule which can bind to another molecule such as a polypeptides or peptide, and should be taken to include, but not be limited to, antibodies, cell surface receptors or phage display molecules.

In addition, nucleotides and peptides having substantial identity to the nucleotide and amino acid sequences of the invention can also be employed in preferred embodiments. Here "substantial identity" means that two sequences, when optimally aligned such as by the programs GAP or BESTFIT (peptides) using default gap weights, or as measured by computer algorithms BLASTX or BLASTP, share at least 50%, preferably 75%, and most preferably 90–95% sequence identity. Preferably, residue positions which are not identical differ by conservative amino acid substitutions. For example, the substitution of amino acids having similar chemical properties such as charge or polarity are not likely to effect the properties of a protein. Non-limiting examples include glutamine for asparagine or glutamic acid for aspartic acid.

In a further aspect, the present invention provides in replicable transfer vectors suitable for use in preparing a polypeptide or peptide of the invention. These vectors may be constructed according to techniques well known in the art, or may be selected from cloning vectors available in the art.

The cloning vector may be selected according to the host or host cell to be used. Useful vectors will generally have the following characteristics:

(a) the ability to self-replicate;
(b) the possession of a single target for any particular restriction endonuclease; and
(c) desirably, carry genes for a readily selectable marker such as antibiotic resistance.

Two major types of vector possessing these characteristics are plasmids and bacterial viruses (bacteriophages or phages). Presently preferred vectors are bacterial, insect or mammalian vectors and may include the following: the pUC, pBlueScript, pGEM, PGEX, pBK-CMV, lambda ZAP, lambda GEM, pEFIRES-P, pUB6/V5/His, pBC1, pADTrack-CMV, pAdenovator, pAdEasy-1, pSFV-PD, pCA3, pBABE, pPIC9, pA0815, pET and pSP series. However, this list should not be seen as limiting the scope of the present invention.

Examples of preferred expression systems are as follows:

1. For an in vitro cell expression system, the 293T cell system with a pEFIRES-P vector (Hobbs S et al., 1998) which confers puromycin resistance may be used. For coexpression of two genes, the aforementioned vector may be modified to change the antibiotic resistance gene to bleomycin resistance. Alternatively, the coexpression of two genes and the selection gene can be achieved by constructing a tricistronic expression vector. A corresponding stably transfected insect cell system can also be used, e.g. the S2 cell system using "DES" vector expression system; (Invitrogen).

2. With respect to expressing GDF's in all tissues of transgenic animals, one approach is to use the pUB6/V5-His A vector to make the constructs. For tissue-specific expression the rat PEPCK 0.6 kb promoter for liver and kidney expression can be included in the construct by replacing the Ubi-C promoter in the pUB6/V5-His A vector with the PEPCK promoter. For GDF expression in mammary tissue another promoter system would be preferred. For this tissue one approach would be to use the bovine β- lactoglobulin gene promoter and/or the bovine αS1 casein promoter (e.g. pBC1 vector (Invitrogen) to drive the expression of the GDFs into milk. For global over-expression in transgenic animals, the CMV enhanced β-actin promoter (Okabe M, et al.; FEBS Letters 407:313–319, 1997) or a modified EFi α-promoter can be used also (Taboit-Dameron F, et al., Transgenic Research 8:223–235, 1998).

Adenoviruses, retroviruses and aiphaviruses are other suitable mammalian expression systems. A typical approach to those skilled in the art is that described by (TC He et al., 1998). With respect to GDF expression the pAd Track-CMV vector or pAdenovator vectors (Obiogene) can be used to make the construct which is then co-transformed with pAd Easy-1 adenoviral plasmid into E. ccli to generate a recombinant adenoviral genome which contains a CMV-promoter driven GDF expression cassette. This recombinant adenoviral genome is then transfected into 293T cells to make the virus stock. Alternative methods for generating adenoviruses can also be used for the same purpose (e.g. PCA3 plasmid based gene transfer (Microbix); or COS-TPC method (Myake S et al., 1996).

3. Non-cytopathogenic Semliki Forest viruses expressing GDF's can be generated using, for example, pSFV-PD vectors as described by Lundstrom et al., Histochem Cell Biol 115:83–91, 2001. Furthermore, retroviral expression systems based on, for example, pBABE vectors, can be used for expressing GDF's in mammalian cells (Morgenstern, JP and Land, H, 1990; Nucleic Acids Res 18:3587–3596).

4. Yeast cells (e.g. Pichia pastoris, Saceharomyces cerevisiae) are another well established expression system to those skilled in the art (C Hadfield, et al., 1993); (MA Romanos et al., 1992). Foe example, the pPIC9 vector (Invitrogen) can be used in Pichia pastoris for the expression of GDF's. For coexpression of two genes, the vector pA0815 (Invitrogen) is a preferred candidate.

Echerichia coli (E. coli) is a standard laboratory expression system in widespread use. For example, the pET expression system (Novagen) can be used to express recombinant mammalian GDF-9 and GDF-9B (steve.lawrence@agresearch.co.nz).

The DNA molecules of the invention may be expressed by placing them in operable linkage with suitable control sequences in a replicable expression vector. Control sequences may include origins of replication, a promoter, enhancer and transcriptional terminator sequences amongst others. The selection of the control sequence to be included in the expression vector is dependent on the type of host or host cell intended to be used for expressing the DNA as would be understood by a person skilled in the art.

The expression vectors useful in the present invention may contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the tre system, major operator and promoter regions of phage lambda, the glycolytic promoters of yeast acid phosphatase, e.g. Pho5, the promoters of the yeast alpha-mating factors, and promoters derived from polyoma, adenovirus, retrovirus, and simian virus, and cytomegalovirus e.g. the early and late promoters of SV40, and other sequences known to control the expression of genes of prokaryotic and eukaryotic cells and their viruses or combinations thereof.

In the construction of a vector it is also an advantage to be able to identify the bacterial clone carrying the vector incorporating the foreign DNA. Such assays include measurable colour changes, antibiotic resistance and the like. In one preferred vector, the β-galactosidase gene is used, which gene is detectable by clones exhibiting a blue phenotype on X-gal plates. This facilitates selection. Once selected, the vectors may be isolated from the culture using standard procedures.

Depending on the host used, transformation and transfection is performed according to standard techniques appropriate to such cells. For prokaryotes or other cells that contain substantial cell walls, the calcium treatment process (Cohen, S N Proceedings, National Academy of Science, USA 2110 (1972)) may be employed. For mammalian cells without such cell walls, the calcium phosphate precipitation method of Graeme and Van Der Eb, Virology 52:546 (1978) or liposomal reagents are preferred.

Upon transformation of the selected host with an appropriate vector the polypeptide encoded can be produced, often in the form of a fusion protein, by culturing the host cells. The polypeptide of the invention may be detected by rapid assays as indicated above. The polypeptide is then recovered and purified as necessary. Recovery and purification can be achieved using any procedures known in the art, for example by absorption onto and elution from an anion exchange resin. This method of producing a polypeptide of the invention constitutes a further aspect of the present invention.

Host cells (including whole animal hosts), transformed, transfected or infected with the vectors of the invention also form a further aspect of the present invention.

In addition, a further aspect of the present invention provides for an antibody, antibody fragment, single cell surface receptor or complex cell surface receptor or phage display molecules binding to a polypeptide or peptide of the invention. The polypeptide or peptide may be present as a monomer, dimer, heterodimer, multimer or a variant thereof.

More specifically, the invention provides methods for producing antibodies against the wild-type (SEQ ID NO: 2) or mutated (SEQ ID NO: 4 and SEQ ID NO: 6) GDF-9B polypeptide sequences as monomers or homodimers or as heterodimers in combination with GDF-9. The antibodies can be used for the characterisation of the wild-type endogenous proteins, or peptide fragments and expressed recombinant proteins, or peptide fragments and for passive immunisation of recipient mammals for the modulation of ovarian follicular growth in vivo.

It will be appreciated by the reader that a further aspect of the invention contemplates the use of the polypeptides of the invention in the preparation of antisera for the detection of other GDF-9B-like peptides.

Polyclonal antibodies may be produced according to the method used by (Koelle et al., 1991) incorporated herein by reference. Useful antibody production protocols are outlined in U.S. Pat. No. 5,514,578. Monoclonal antibodies may be produced by methods known in the art. These methods include the immunological method described by (Kohler and Milstein, 1975) as well as the recombinant DNA method described by (Huse et al., 1989).

In a further embodiment, the invention provides a method of manipulating ovarian follicular growth in cells in culture and/or transgenic animals. By overexpression of GDF-9B homodimers and GDF-9B/GDF-9 heterodimers, the timing and level of expression of specific ovarian follicular protein genes may be altered in cultured cells or transgenic animals, for example GDF-9B homodimers or GDF-9B/GDF-9 heterodimers encoding sequences may be inserted into a gene cassette under the control of a specific promoter or a promoter that expresses in all cell types (see examples below) (constitutive expression). This cassette also comprises 3' flanking DNA that could stabilise the mRNA and may optionally comprise downstream regulatory sequences. This DNA cassette could be introduced into the genome of mammals by micro injection of the DNA into the pronuclei of eggs (as described in L'Huillier et al., 1996) which are subsequently transferred back to recipient animals and allowed to develop to term. This technique for the production of transgenic animals is described by (Hogan et al., 1996). Transgenic animals may be produced by transfection of cells in culture derived from an embryo, or foetal or adult tissues; followed by nuclear transfer and embryo transfer to recipient animals. Alternatively the gene cassette may be bound to mammalian sperm and delivered to the egg via in vitro or in vivo fertilisation to produce a non-human transgenic animal. Manipulation of the developmental regulation or the level of expression of GDF-9B homodimers or GDF-9B/GDF-9 heterodimers may be used to alter the level of ovarian follicular protein synthesis or production.

The invention also includes adenovirus-based gene therapy techniques for expressing GDF-9B and GDF-9/GDF-9B in cell cultures, organ cultures and whole experimental animals for manipulating ovarian follicular protein synthesis or production.

Non-limiting examples illustrating the invention will now be provided. It will be appreciated that the above description is provided by way of example only and variations in both the materials and techniques used which are known to those persons skilled in the art are contemplated.

EXAMPLES

Example 1

Isolation of Wildtype Ovine GDF-9B DNA and Identification of Mutated Ovine GDF-9B DNA Sequences Different combinations of oligonucleotide primers derived from human/mouse/rat GDF-9B sequences previously cloned by us were used in PCR on genomic sheep DNA for obtaining fragments of the ovine GDF-9B gene for sequencing. Functional primer pairs were used for obtaining wild-type sheep genomic clones from arrayed libraries and for obtaining cDNA sequence from wild-type ovine ovarian cDNA. The sequence from the full coding regions of Inverdale and Hanna was obtained by sequencing relevant PCR fragments obtained from the respective genomic DNA's. The wildtype GDF-9B sequence is disclosed here as SEQ ID NO: 1, Inverdale as SEQ ID NO: 3, and Hanna as SEQ ID NO: 5.

Example 2

Production of Specific Antibodies and Demonstration of Natural Homodimeric GDF-9B and Heterodimeric GDF-9B/GDF-9 Proteins in Mammalian Ovaries Antigens for immunising mammals or birds are generated using nucleotide sequences disclosed in the invention as SEQ ID NO: 1, SEQ ID NO: 3, and SEQ ID NO: 5 or variants thereof in operative association with an expression control sequence enabling expression of the protein in *E. coli*. Yet as another approach, anti-peptide antibodies directed against specific peptide sequences from SEQ ID NO: 2, SEQ ID NO: 4, SEQ ID NO: 6 or variants thereof are generated. Immunoreactivity can be assessed by standard methods (e.g. ELISA) and/or to obtain specific IgGs recognising GDF-9B homodimers and GDF-9B/GDF-9 protein heterodimers from natural sources and cell/tissues overexpressing the respective recombinant proteins.

Previous evidence by the inventors' group (e.g. Aaltonen et al. (1999) and Jaatinen et al., 1999) show the presence of GDF-9 mRNA and protein in oocytes of preantral follicles in rodents and primates. Here we show evidence by immunocytochemistry using a mouse antibody for the presence of GDF-9B protein in sheep ovaries (FIG. 2). The immunohistochemical methodology was similar to that described by Tisdall et al. (1999) Stem cell factor and c-kit gene expression and protein localisation in the sheep ovary during fetal development, J Reprod Fert 116:277. The only exception was that a tyramide signal amplification step was also included in the present study (TSA Biotin System, NEN Life Science Products). The mouse antibody M10 was generated after an *E. coli* derived mature ovine GDF-9B peptide (0.2 mg) was injected in Freunds complete adjuvant (FCA), intraperitoneally (i.p.) and at 2 weekly intervals boosted with 0.1 mg antigen i.p. and subsequently with 0.05 mg antigen in a Span/Tween/oil mixture and the animal sacrificed 1 week after the final booster and serum collected.

Collectively these and other data show that both the mRNA and protein for GDF-9 and GDF-9B are present in oocytes of mammals (Aaltonen et al., 1999; Galloway et al., 2000).

Evidence that antipeptide antibodies directed against specific peptide sequences affect mammalian ovarian activity is shown in Table 1.

TABLE 1

Ovulation rate in sheep following administration of plasma containing antibodies to keyhole limpet haemocyanin (KLH) conjugated to GDF-9B peptide

| Treatment | Mean Ovulation Rate (range) |
| --- | --- |
| Anti-KLH | 1.6 |
| (n = 5 animals) | (1–2) |
| Anti-GDF-9B peptide | 0.2* |
| (5) | (0–1) |

*$p < 0.05$ (students t-test)

In this study 10 female sheep had their oestrous (i.e. ovarian) cycles synchronised using prostaglandin $F_2\alpha$ (Estrumate, 125 μg i.m.). All animals were observed to show synchronised oestrus following markings with vasectomised rams. On day 5 of the subsequent luteal phase, 5 ewes were administered with a pooled plasma recovered from another flock of ewes that had been immunised on 7 consecutive monthly occasions with a 15 mer GDF-9B peptide conjugated to keyhole limpet haemocyanin (KLH). The pooled sera contained high titre antibodies to GDF-9B as assessed by ELISA assay using a full-length *E. coli* expressed GDF-9B as antigen. The other 5 ewes were administered with a pooled plasma to KLH recovered from a separate flock of ewes that had been immunised also on 7 consecutive monthly occasions. The pooled plasma from these animals did not contain detectable GDF-9B antibody.

Antibody levels were measured by an ELISA procedure after the sheep plasmas were diluted 1:50000. The ELISA method involved coating a 96-well plate with 100 ng/well of an *E. coli* expressed full-length GDF-9B and incubation with 100 μl of diluted sheep plasma and 100 μl of assay buffer, after appropriate blocking treatment and successive washes. After incubation with the sheep plasma and several washes, rabbit anti-sheep-HRP was added for 1 h at 37° C. The wells were then washed and developed with o-phenylenediamine plus hydrogen peroxide with development being stopped with sulphuric acid.

The ewes were each given 100 ml of sterile plasma intravenously and 4 days later administered with a second prostaglandin $F_2\alpha$ injection to synchronise oestrus. The ovulation rates were examined by laparoscopy 14 days after administration of plasma.

In our previous patent no. 500844 we demonstrated a significant perturbation in ovarian follicular development in mice when the animals were immunised with an *E. coli* derived mature ovine GDF-9B. In this study 10 female mice were immunised intraperitoneally (i.p.) with the *E. coli*-derived mature ovine GDF-9B protein (0.2 mg) in Freunds complete adjuvant (FCA) (0.2 ml), and another 10 female mice were immunised with bovine alpha lactalbumin (0.2 mg) in FCA (0.22 ml) i.p. to serve as controls. Subsequently, 3 booster injections of the appropriate antigens (0.1 mg at first booster and 0.05 mg at second and third booster) were given at 2 week intervals in a Span/Tween/oil mixture and the animals sacrificed 1 week after the final booster.

Here we provide evidence for these GDF-9B immunised mice that the exogenous biological activities of both GDF-9 and GDF-9B are likely to be affected since these animals contained cross-reacting antibodies to both growth factors (Table 2).

TABLE 2

Mean (±s.e.m.) antibody levels in mouse plasma following immunisation with bovine alpha lactalbumin or ovine GDF-9B. The values presented show the absorbance at 490 nm which represents the levels of antibody to GDF-9B or GDF-9.

| Treatment | GDF-9B | GDF-9 |
|---|---|---|
| Bovine α-lactalbumin | <0.060 | <0.060 |
| GDF-9B | 2.177 (±0.163) | 0.590 (±0.058) |

Thus we assert that procedures that lead to the modulation of endogenous GDF-9 and GDF-9B will alter ovarian function.

Further evidence in support of our claim that modulating homodimeric GDF-9B or GDF-9 and GDF-9B either as homodimeric mixtures or heterodimers is provided by our novel findings following the immunisation of sheep (3–5 per treatment group) against KLH (control), GDF-9B peptide conjugated to KLH or GDF-9 peptide conjugated to KLH. The animals were subjected to 7 consecutive monthly immunisations, the ovaries recovered after slaughter and thereafter the ovarian volumes and numbers of types 1, 1 *a* and 2 follicles were assessed by standard morphometric procedures (Smith et al., 1997). In addition the presence or absence of antral follicles were noted. These results are summarised in Table 3.

TABLE 3

Mean ovarian volumes and numbers of Types 1–2, 3–4 and antral follicles following immunisation of sheep with KLH, KLH conjugated to GDF-9B peptide or to GDF-9 peptide.

| Treatment | Ovarian volume (mean range) | Number of Type 1–2 follicles (mean range) | Number of Type 3–4 follicles (mean range) | Number of antral follicles (mean range) |
|---|---|---|---|---|
| KLH (3) | 486 (353–651) | 15180 (11623–17433) | 63 (61–65) | 28 (22–37) |
| GDF-9B Peptide-KLH (5) | 296 (149–488) | 8147 (3221–13786) | 0 | 0 |
| GDF-9 Peptide-KLH (2) | 284 (248–303) | 16278 (10152–25745) | 0 | 4 (0–11) |

For these studies the GDF-9B peptide sequence was SEVPGPSREHDGPESC (SEQ ID NO 17) and the GDF-9 peptide sequence was KKPLVPASVNLSEYFC (SEQ ID NO 18). The Romney ewes were injected with 0.4 mg/ewe of KLH or KLH-GDF-9B peptide or KLH-GDF-9 peptide in Freund's complete adjuvant. Subsequently at monthly intervals on 6 occasions, the animals were boosted with further antigen (0.2 mg/ewe on each occasion) in a Span/Tween/oil mixture (s.c.).

The results show that relative to the controls (KLH immunisations): (1) GDF KLH and GDF-9B-KLH immunisations each can inhibit antral follicle development thereby demonstrating that both GDF-9 and GDF-9B are essential for normal follicular development in some mammals.

Example 3

Expression of Recombinant Homodimeric GDF-9B and Heterodimeric GDF-9B/GDF-9 Protein in Mammalian Cells In Vitro and In Vivo Expression constructs generated in plasmid vectors containing nucleotide sequences disclosed in the invention as SEQ ID NO: 1, SEQ ID NO: 3, and SEQ ID NO: 5 or variants thereof in operative association with an expression control sequence (CMV, EF1, and mammary specific promoter sequences) are transfected/transferred to mammalian cells and stable clones are selected using an antibiotic selection marker. For optimising the processing of the expressed recombinant polypeptide sequence the furin processing site is mutated and an auxiliary expression cassette driving the overexpression of the furin protease in the producer cells is introduced.

As an example of an effective mammalian expression system for producing oGDF-9B homodimeric protein we have generated human 293T cell lines transfected with the pEFIRES-P vector containing the rat GDF-9B proregion (Jaatinen et al., Mol Cell Endocrinol. 156:189–93, 1999) fused to an ovine GDF-913 mature region sequence (SEQ ID NO: 1 and NO: 2). The furin processing site had been engineered to contain the effectively cleaved RRRR sequence. Cells selected to resist 120–150 ug/ml puromycin were cultured in HamF12/DMEM under serum free conditions for 4 days to produce ovine GDF-9B into the supernatant which was subsequently used in bioassay as described in Example 4.

To gain biochemical evidence for physical heterodimerisation of sheep GDF-9B with GDF-9 the following approach was used. A similar rat/sheep chimeric GDF-9B open reading frame as described above but containing a C-terminal 8 amino acid FLAG epitope was cloned into pSFV-PD Semliki Forest Virus vector and a high titre virus stock of SFV-PD-oGDF-9B-FLAG was generated in BHK cells as described in Lundstrom et al, Histochem Cell Biol 115: 83–919 2001). A high titre SFV-PD-oGDF-9B-FLAG virus was seen to very effectively infect human 293T cells and cause high expression of oGDF-9B-FLAG in these cells. After infection, during a 4 day culture processed oGDF-9B-FLAG was secreted to medium and the protein was easily visualised as a 18 kd band in Western blot analysis using anti-FLAG M2 antibody. For co-expression of ovine GDF-9B-FLAG with ovine GDF-9 another 293T cell line was generated using a pEFIRES-P vector containing an open reading frame encoding a prepro GDF-9 polypeptide. Parental 293T cells and 293T cells stably 22 expressing oGDF-9 were infected with equal amounts of SFV-PD-oGDF-9B-FLAG viruses and supernatants were collected after 4 days in culture. One ml of supernatants from uninfected and SFV-PD-oGDF-9B-FLAG infected cells were subjected to immunoprecipitation with 1 μg/ml anti FLAG-M2 antibodies and complexes were recovered with protein G agarose. Eluates were evaluated in Western blots using anti-FLAG-M2 antibodies and anti GDF-9 antibodies. Although anti FLAG M2 antibodies do not react with ovine GDF-9, an immunoreactive 20 kd GDF-9 mature peptide was seen in supernatants of GDF-9 expressing cells that had been infected with SFV-PD-oGDF-9B-FLAG viruses and immunoprecipitated with anti FLAG M2 antibodies. These coimmunoprecipitation experiments indicate a direct physical interaction of recombinantly expressed ovine GDF-9B and GDF-9 and confirm the existence of sheep GDF-9/GDF-9B heterodimers.

Methods are described for over-expressing nucleotide sequences disclosed in the invention as SEQ ID NO: 1, SEQ ID NO: 3, and SEQ ID NO: 5 or variants thereof in several extraovarian sites in transgenic animals for mimicking systemic administration of recombinant homodimeric GDF-9B and heterodimeric GDF-9B/GDF-9 proteins. The relevant GDF encoding sequences are either expressed separately or co-expressed in operative association with expression control sequences. Effects of GDF-9B homodimers and GDF-9B/GDF-9 heterodimers on ovarian follicular growth in these transgenic animals are assessed by morphometric measurements or hormonal assays. This approach provides a general method for altering ovulation rate in transgenic animals. Production of GDF's into milk by mammary gland directed overexpression provides an alternative method of producing large amounts of reagent for medical or pharmaceutical purposes. This approach is not injurious to the health of the transgenic animal as no contraindications have been observed.

A method is described for effectively transferring an expression cassette composed of nucleotide sequences disclosed in the invention as SEQ ID NO: 1, SEQ ID NO: 3, and SEQ ID NO: 5 or variants thereof in operative association with an expression control sequence (CMV promoter) in a recombinant adenovirus into recipient cell or organ cultures or recipient animals for altering follicular growth in vitro or in vivo. For example, the methods allow systemic infection of recipient mammals with GDF-9B and GDF-9 expression cassette bearing adenoviruses concentrating into the livers of the host and allowing high levels of liver derived recombinant proteins to be released to the circulation. Effects on ovarian follicular growth may be assessed by one or more criteria such as laparoscopy, morphometric measurements or hormonal assays. A similar in vivo viral transfer of GDF-9B And GDF-9 sequences and transcriptional units can be achieved with alphaviruses or 23 retroviruses. These viral approaches offer ways of testing the bioactivity of different GDF-9B and GDF-9 gene constructs in vivo and also provide alternative ways of immunising animals against GDF-9B and GDF-9.

Example 4

Measurement of the Biological Activity of Homodimeric GDF-9B and Heterodimeric GDF-9B/GDF-9 Proteins in Ovarian Cell Cultures For assessing the biological activity of proteins expressed from the nucleotide sequences disclosed in the invention as SEQ ID NO: 1, SEQ ID NO: 3, and SEQ ID NO: 5 or variants thereof ovarian cell and organ culture models may be used.

An example of assessing the biological activity of homodimeric GDF-9B is shown in Table 4 below whereby a partially purified recombinant (r) ovine (O)GDF-9B extract is assessed by measurement of [$^3$H] thymidine incorporation by isolated ovine granulosa cells during a 48 h incubation at 37° C. The results show that the roGDF-9B caused a 1.9-fold increase in tritiated thymidine incorporation by granulosa cells indicating that the roGDF-9B was biologically active. To obtain the granulosa cells, ovaries were recovered from ewes, follicles (1–2.5 mm diameter) dissected free and the cells isolated and separated from theca and oocyte-cumulus complexes. The cells were washed and resuspended in fresh media at a final concentration for bioassay of $1 \times 10^5$ viable cells per well.

TABLE 4

Mean ± s.e.m. increase in [$^3$H] thymidine incorporation in ovine (o) granulosa cells after exposure to roGDF-9B or control media (n = 3 separate experiments)

| Treatment | [$^3$H] thymidine incorporation (cpm) |
|---|---|
| control | 3256 ± 283 |
| Rec Ovine (o)-GDF-9B | 6291 ± 503*** |

RoGDF-9B was produced by transfected 293T cells and partially purified using heparin-sepharose chromatography and the protein eluted with 0.5 M NaCl and dialysed overnight against tissue culture media. The control for this experiment was media exposed to non-transfected 293T cells and subjected to heparin-sepharose chromatography, NaCl elution and dialysis.
***p < 0.001, ANOVA

DISCUSSION

The known human GDF-9B sequence and oligonucleotide primers derived thereof enabled the inventors to determine the sheep GDF-9B genomic and cDNA sequences and to assess the expression of GDF-9B transcripts in sheep ovaries (Galloway et al., 2000).

From literature it appears that GDF-9 is needed for granulosa cell mitogenesis and thecal cell differentiation. Indeed, recombinant rat GDF-9 is able to stimulate rat follicular growth in vitro (Hayashi et al., 1999) as well as the proliferation of rat granulosa cells in culture (Vitt et al., 2000). Recombinant GDF-9 also regulates steroidogenesis and gonadotrophin receptor expression in mouse and rat granulosa cells (Elvin et al., 1999; Vitt et al., 2000). Furthermore, GDF-9 stimulates inhibin B production in human granulosa cells in culture (Vuojolainen et al., in preparation). These recent studies clearly demonstrate that GDF-9 homodimers have potent effects on follicular growth and differentiation in several mammals but before the invention described herein nothing has been known on the possible biological effect of GDF-9B in the ovary.

In our earlier New Zealand patent specification no. 500844 the present inventors showed that the Inverdale gene maps to a sheep X-chromosome region containing genes syntenic to Xp11.2–11.4 in human (Galloway et al., 2000) and determined whether GDF-9B gene is affected in these animals, showing that the Inverdale gene is actually an inactivated form of the sheep GDF-9B gene. In Inverdale animals the T nucleotide at position 92 nucleotides beyond the mature peptide processing site has become an A residue, converting the codon GTC to GAC causing the substitution of the amino acid valine (V) to aspartic acid (D). In all TGF-β family members this very amino acid is either valine, isoleucine or leucine which all represent hydrophobic residues in contrast to the negatively charged aspartic acid. This amino acid substitution causes a change in the surface charge of the very area of the molecule which is involved in the dimerisation process as suggested from the crystal structures of TGF-β2, BMP-2 and BMP-7 (Schlunegger and Grutter, 1993; Griffith et al., 1996; Scheufler et al., 1999). The invention of New Zealand 500844 also provides evidence for a second GDF-9B gene mutation identified in another flock of sheep, Hanna, having exactly the same heterozygous and homozygous gene carrier phenotypes as Inverdale ewes. Hanna animals present with a C to T nucleotide point mutation at position 67 nucleotides beyond the mature peptide processing site introducing a premature stop codon at the place of a glutamine (Q) residue. This change will cause a major truncation of the mature peptide region causing inactivation of the protein product. Crosses between the Inverdale and Hanna families lead to 50% infertile females proving that both mutations clearly inactivate the GDF-9B gene product.

REFERENCES

Aaltonen J, Laitinen M, Vuojolainen K, Jaatinen R, Horelli-Kuitunen N, Seppa L, Louhio H, Tuuri T, Sjoberg J, Butzow R, Hovatta O, Dale L, Ritvos 0: Human growth differentiation factor-9 (GDF-9) and its novel homolog GDF-9B are expressed during early folliculogenesis. J Clin Endocrinol Metab 84: 2744–2750,1999

Braw-Tal R, McNatty K P, Smith P, Heath D A, Hudson, N L, Phillips D J, McLeod B J, Davis G H: Ovaries of ewes homozygous for the X-linked Inverdale gene (FecXI) are devoid of secondary and tertiary follicles but contain many abnormal structures. Biol Reprod 49:895–907, 1993.

C Hadfield, K K Raina, K Shashi-Menon, R C Mount (1993) The expression and performance of cloned genes. Yeast Mycol Res 9, 897–944

Daopin S, Piez K A, Ogawa Y, Davies D R: Crystal structure of transforming growth factor-beta 2: an unusual fold for the superfamily. Science 257:369–373, 1992.

Davis G H, McEwan J C, Fennessy P F, Dodds K G, Farquhar P A: Evidence for the presence of a major gene influencing ovulation rate on the X chromosome of sheep. Biol Reprod 44:620–624, 1991.

Davis G H, McEwan J C, Fennessy P F, Dodds K G, McNatty K P, O WS: Infertility due to bilateral ovarian hypoplasia in sheep homozygous (FecXI FecXI) for the Inverdale prolificacy gene located on the X chromosome. Biol Reprod 46:636–640, 1992

Davis G H, McEwan J C, Fennessy P F, Dodds K G: Discovery of the Inverdale gene (FecX). Proc N Z Soc Anim Prod 95:289–290,1995.

Dong J, Albertini D F, Nishimori K, Kumar T R, Lu N, Matzuk M M: Growth differentiation factor-9 is required during early ovarian folliculogenesis. Nature 383:531–535, 1996

Dube J L, Wang P, Elvin J, Lyons K M, Celeste A J, Matzuk M M: The bone morphogenetic protein 15 gene is X-linked and expressed in oocytes. Mol Endocrinol 12:1809–1817, 1998

Elvin J A, Clark A T, Wang P, Wolfman N M, Matzuk M M: Paracrine actions of growth differentiation factor-9 in the mammalian ovary. Mol Endocrinol 13:1035–1048, 1999

Galloway S M, McNatty K P, Cambridge L M, Laitinen M P E, Juengel J L, Jokiranta T S, McLaren R J, Luiro K, Dodds K G, Montgomery G W, Beattie A E, Davis G H, Ritvos O: Mutations in an oocyte-derived growth factor gene (BMP15) cause increased ovulation rate and infertility in a dosage-sensitive manner. Nature Genetics 25:279–283, 2000.

Griffith D L, Keck P C, Sampath T K, Rueger D C, Carlson W D: Three-dimensional structure of recombinant human osteogenic protein 1: structural paradigm for the transforming growth factor beta superfamily. Proc Natl Acad Sci USA 93:878–883, 1996.

Hanna M M: Living with the Inverdale gene (FecX) in a Romney flock. Proc NZ Soc Anim Prod 55:296–297, 1995.

Hayashi M, McGee E A, Min G, Klein C, Rose U M, van Duin M, Hsuch A J: Recombinant growth differentiation factor-9 (GDF-9) enhances growth and differentiation of cultured early ovarian follicles. Endocrinology 140:1236–1244, 1999

Hobbs S, Jitrapakdee S, Wallace J C (1998) Development of a bicistronic vector driven by the human polypeptide chain elongation factor 1 alpha promoter for creation of stable mammalian cell lines that express very high levels of recombinant proteins. Biochem Biophys Res Commun 252, 368–372

Hogan et al (1; In: Manipulating the mouse embryo, Cold Spring Harbor Laboratory. Press 1996)

Huse et al., Science 246: 1275–1281 (1989).

Jaatinen S. et al. 1999 Molecular and Cell Endocrinology 156:189–193.

Koelle et al., Cell 67: 59–77, 1991.

Kohler and Milstein in Nature 256: 495–497 (1975).

Juengel et al. (2000) Gene expression in abnormal ovarian structures of ewes homozygous for the Inverdale prolificacy gene, Biol Reprod, 62, 1467–1478.1

Laitinen M, Vuojolainen K, Jaatinen R, Ketola I, Aaltonen J, Lehtonen E, Heikinheimo M, Ritvos O: A novel growth differentiation factor-9 (GDF-9) related factor is co-expressed with GDF-9 in mouse oocytes during folliculogenesis. Mech Dev 78:135–140, 1998.

L'Huillier et al PNAS 93; 6698–6703 (1996).

MA Romanos, CA Scorer, JJ Glare (1992) Foreign gene expression in yeast: a review. Yeast 8, 423–488.

McGrath SA, Esquela AF, Lee SJ: Oocyte-specific expression of growth differentiation factor Mol Endocrinol 9:131–136, 1995.

McNatty KP, Smith P, Hudson NL, Heath DA, Tisdall DJ, O WS, Braw-Tal R: Development of the sheep ovary during fetal and early neonatal life and the effect of fecundity genes. J Reprod Fertil Suppl 49:123–135, 1995.

McPherron AC, Lee SJ: GDF-3 and GDF-9: two new members of the transforming growth factor-beta superfamily containing a novel pattern of cysteines. J Biol Chem 268: 3444–3449, 1993.

Miyake S, Makimura M, Kanegae Y, Harada S, Sato Y, Takamori K, Tokuda C, Saito I. Efficient generation of recombinant adenoviruses using adenovirus DNA-terminal protein complex and a cosmid bearing the full-length virus genome. Proc Natl Acad Sci U S A. 93:1320–1324,1996.

Neilsen H., Engelbrecht J, Brunak S, von Heijne G: Identification of prokaryotic and eukaryotic signal peptides and prediction of their cleavage sites. Protein Eng 10: 1–6.

Scheufler C, Sebald W, Hulsmeyer M: Crystal structure of human bone morphogenetic protein-2 at 2.7 A resolution. J Mol Biol 287:103–115, 1999.1

Schlunegger MP, Grutter MG: An unusual feature revealed by the crystal structure at 2.2 A resolution of human transforming growth factor-beta 2. Nature 358:430–434, 1992.

SlSchlunegger MP, Grutter MG: Refined crystal structure of human transforming growth factor beta 2 at 1.95 A resolution. J Mol Biol 231:445–458, 1993.

Shackell GH, Hudson NL, Heath DA, Lun S, Shaw L, Condell L, Blay LR, McNatty KP Plasma gonadotrophin concentrations and ovarian characteristics in Inverdale ewes that are heterozygous for a major gene (FecX[1]) on the X chromosome that influences ovulation rate. Biol Reprod 48:1150–1156 1993.

Smith P, O WS, Corrigan KA, Smith T, Lundy T, Davis GH, MeNatty KP: Ovarian morphology and endocrine characteristics of female sheep fetuses that are heterozygous or homozygous for the Inverdale prolificacy gene (fecX1). Biol Reprod 57:1183–1192, 1997.

TC He, S Zhou, LT da Costa, J. Yu, KW Kinzler, B. Vogelstein (1998) A simplified system for generating recombinant adenoviruses. Proc Natl Acad Sci USA 95, 2509.

Tisdall et al. (1999) Stem cell factor and c-kit gene expression and protein localisation in the sheep ovary during fetal development, J Reprod Fert 116: 277–291.

Vitt UA, Hayashi M, Klein C, Hsueh AJW: Growth differentiation factor-9 stimulates proliferation but suppresses the follicle-stimulating hormone-induced differentiation of culture granulosa cells from small antral and preovulatory rat follicles. Biol Reprod, 62, 370–377, 2000.

Vuojolainen K, Bondestarn J, Hayashi M, Raivio T, Evans L, Groome NP, Hsueh AJW, Ritvos O. GDF-9 regulates inhibin B production in cultured human granulosa-luteal cells. Manuscript in preparation.

What is claimed is:

1. An isolated full-length GDF-9B polypeptide comprising an amino acid sequence selected from the group consisting of:
   a) SEQ ID NO: 2 and
   b) a functional variant of GDF-9B with at least 95% sequence identity to SEQ ID NO: 2, wherein saidGDF-9B polypeptide or said functional variant is able to enhance ovarian follicular growth.

2. A method for enhancing ovarian follicular growth in vivo or in vitro, comprising administering a pharmaceutical composition comprising GDF-9B homodimers or GDF-9B/GDF-9 heterodimers, wherein said homodimers and heterodimers comprise a polypeptide according to claim 1.

3. The method of claim 2, wherein said composition further comprises supplementary gonadotrophins or ovarian growth factors selected from the group consisting of IGF-1, kit ligand (stem cell factor), epidermal growth factor and TGFβ agonists/antagonists.

4. An isolated polypeptide, wherein said polypeptide is a homodimeric mature GDF-9B polypeptide having subunits comprising the amino acid sequence of SEQ ID NO: 2 or an amino acid sequence with at least 95% sequence identity to SEQ ID NO: 2 that is able to enhance ovarian follicular growth.

5. An isolated polypeptide, wherein said polypeptide is a heterodimeric polypeptide having one subunit selected from the group consisting of:
   a) a mature GDF-9B polypeptide comprising the amino acid sequence of SEQ ID NO: 2, and
   b) a mature GDF-9B polypeptide with at least 95% sequence identity to SEQ ID NO: 2 that is able to enhance ovarian follicular growth and
   c) a second subunit selected from the group consisting of a mature GDF-9 polypeptide and
   d) a mature GDF-9 polypeptide with at least 95% sequence identity to GDF-9 that is able to enhance ovarian follicular growth.

6. A composition comprising an agent selected from the group consisting of:
   a) a homodimeric polypeptide having subunits comprising a GDF-9B polypeptide comprising the amino acid sequence of SEQ ID NO: 2 that is able to enhance ovarian follicular growth;
   b) a heterodimeric polypeptide having subunits comprising a GDF-9B polypeptide comprising the amino acid sequence of SEQ ID NO: 2 and a GDF-9 polypeptide and
   c) a heterodimeric polypeptide comprising subunits with at least 95% identity to GDF-9B comprising SEQ ID NO: 2 and GDF-9, respectively, that is able to enhance ovarian follicular growth;
   together with a pharmaceutically or veterinarily acceptable carrier, adjuvant or diluent.

7. The composition of claim 6, wherein the composition further comprises supplementary gonadotropins.

8. The composition of claim 6, wherein the composition further comprises an additional ovarian growth factor selected from the group consisting of IGF-1, kit ligand (stem cell factor), epidermal growth factor and TGFβ agonists/antagonists.

9. The composition of claim 7, wherein the composition further comprises an additional ovarian growth factor selected from the group consisting of IGF-1, kit ligand (stem cell factor), epidermal growth factor and TGFβ agonists/antagonists.

10. A method for enhancing ovarian follicular growth, in vitro or in vivo, in a female mammal comprising administering to said female mammal a composition selected from the group consisting of:
    a) the composition of claim 6;
    b) the composition of claim 6, wherein the composition further comprises supplementary gonadotrophins;
    c) the composition of claim 6, wherein the composition further comprises an ovarian growth factor selected from the group consisting of IGF-1, kit ligand (stem cell factor), epidermal growth factor and TGFβ agonists/antagonists; and
    d) the composition of c) above, wherein the composition further comprises supplementary gonadotrophins,
    whereby the administered composition enhances ovarian follicular growth.

11. A method for enhancing mammalian ovarian cell growth or maturation in vitro comprising administering to isolated mammalian ovarian cells a composition selected from the group consisting of:
    a) the composition of claim 6;
    b) the composition of claim 6, wherein the composition further comprises supplementary gonadotrophins
    c) the composition of claim 6, wherein the composition further comprises an ovarian growth factor selected from the group consisting of IGF-1, kit ligand (stem cell factor), epidermal growth factor and TGFβ agonists/antagonists; and
    d) the composition of c) above, wherein the composition further comprises supplementary gonadotrophins,
    whereby the administered compositions enhances isolated ovarian cell growth or maturation.

12. The composition of claim 6, further comprising a homodimeric polypeptide having subunits comprising a GDF-9 polypeptide or a GDF-9 polypeptide with at least 95% sequence identity to GDF-9 that is able to enhance ovarian follicular growth.

13. A method for assessing the activity of GDF-9B homodimers, GDF-9B/GDF-9 heterodimers, or the combination thereof, wherein said homodimers and heterodimers comprise a polypeptide according to claim 1, comprising:

a) adding an effective amount of said GDF-9B homodimeric polypeptide, GDF 9B/GDF-9 heterodimeric polypeptide, or the combination thereof to an ovarian cell or organ culture; and b) conducting a bioassay on said cell or organ culture to assess the biological activity of said homodimeric and heterodimeric polypeptides.

* * * * *

SEQUENCE LISTING

```
<160> NUMBER OF SEQ ID NOS: 20

<210> SEQ ID NO 1
<211> LENGTH: 2044
<212> TYPE: DNA
<213> ORGANISM: Ovis aries
<220> FEATURE:
<221> NAME/KEY: 5'UTR
<222> LOCATION: (1)...(234)
<220> FEATURE:
<221> NAME/KEY: misc_feature
<222> LOCATION: (235)...(237)
<223> OTHER INFORMATION: atg start codon
<220> FEATURE:
<221> NAME/KEY: misc_feature
<222> LOCATION: (208)...(210)
<223> OTHER INFORMATION: in frame 5' atg codon
<220> FEATURE:
<221> NAME/KEY: CDS
<222> LOCATION: (235)...(559)
<220> FEATURE:
<221> NAME/KEY: sig_peptide
<222> LOCATION: (235)...(309)
<220> FEATURE:
```

```
<221> NAME/KEY: CDS
<222> LOCATION: (1175)...(2028)
<220> FEATURE:
<221> NAME/KEY: intron
<222> LOCATION: (560)...(1174)
<220> FEATURE:
<221> NAME/KEY: mat_peptide
<222> LOCATION: (1654)...()
<220> FEATURE:
<221> NAME/KEY: misc_feature
<222> LOCATION: (784)...()
<223> OTHER INFORMATION: n = a, or g, or c, or t
<220> FEATURE:
<221> NAME/KEY: unsure
<222> LOCATION: (784)...()
<223> OTHER INFORMATION: n = approximately 5.4 kb of unsequenced intron
<220> FEATURE:
<221> NAME/KEY: misc_feature
<222> LOCATION: (2029)...(2031)
<223> OTHER INFORMATION: tga stop codon
<220> FEATURE:
<221> NAME/KEY: 3'UTR
<222> LOCATION: (2032)...(2044)

<400> SEQUENCE: 1
```

| | | |
|---|---|---|
| ctgctgtttc tgtttgtttg atgcaaagag gacaatttag aagacctctt tttggttcag | 60 |
| gagatcctac cagaggaaga aacataggac ctgcctgcca gcctttcatt tttccttgcc | 120 |
| ctatcctttg tggtagtgga gcctggatgc tgttacccat gtaaaaggaa aggtttaaag | 180 |
| cgttatcctt tgggctttta tcagaacatg ttgctgaaca ccaagctttt caag atg | 237 |
| | Met |
| | -25 |

```
gtc ctc ctg agc atc ctt aga atc ctt ctt tgg gga ctg gtg ctt ttt    285
Val Leu Leu Ser Ile Leu Arg Ile Leu Leu Trp Gly Leu Val Leu Phe
        -20              -15              -10 atg gaa cat agg gtc caa atg aca cag gta ggg cag ccc tct att gcc    333
Met Glu His Arg Val Gln Met Thr Gln Val Gly Gln Pro Ser Ile Ala
         -5               1                5 cac ctg cct gag gcc cct acc ttg ccc ctg att cag gag ctg cta gaa    381
His Leu Pro Glu Ala Pro Thr Leu Pro Leu Ile Gln Glu Leu Leu Glu
        10               15               20 gaa gcc cct ggc aag cag cag agg aag ccg cgg gtc tta ggg cat ccc    429
Glu Ala Pro Gly Lys Gln Gln Arg Lys Pro Arg Val Leu Gly His Pro
25               30               35               40 tta cgg tat atg ctg gag ctg tac cag cgt tca gct gac gca agt gga    477
Leu Arg Tyr Met Leu Glu Leu Tyr Gln Arg Ser Ala Asp Ala Ser Gly
            45               50               55 cac cct agg gaa aac cgc acc att ggg gcc acc atg gtg agg ctg gtg    525
His Pro Arg Glu Asn Arg Thr Ile Gly Ala Thr Met Val Arg Leu Val
             60               65               70 agg ccg ctg gct agt gta gca agg cct ctc aga g gtgagttatc          569
Arg Pro Leu Ala Ser Val Ala Arg Pro Leu Arg
         75               80
```

| | | |
|---|---|---|
| atactatatt gttctggtgg gaggggggga gaaaatgggg aagaaaagtg tagaaaaaag | 629 |
| tggatctgtc agtttttctgt caggcttcac attgcctaca gggtaggtgg ttttcaaaag | 689 |
| atggcaccct tggagaaacc tggctccaaa tttgcttccc tttagggctc caatttaaga | 749 |
| acagattgcc ttgggccctc cctgaggact ttctnagttc tgtatttgag gtgttttttct | 809 |
| ccgtctaggg gtatgagtga tctaaaaatg agccacaatt tgtcatctta agggaaaaag | 869 |
| acttggactc aaatctttat tctaacaaac actggcttgt gtgtcctctg gcatagcttc | 929 |
| tctgagcttc agtttcctcg tctgcaaaat gggaatagca actatctcat aaggctattg | 989 |
| tggattcaag agcaaatgca tgtaaagcat ctaatacatt atataagtgc tcaatagatc | 1049 |

-continued

```
gctattatga tcttaaattc atctcaaggc tgcttgtcag tttgtactga gcaggtctgt   1109
tagagagact aaggctagga tataagaagc taacgctttg ctcttgttcc ctcttactaa   1169 tgcag gc tcc tgg cac ata cag acc ctg gac ttt cct ctg aga cca aac   1218
      Gly Ser Trp His Ile Gln Thr Leu Asp Phe Pro Leu Arg Pro Asn
          85                  90                  95 cgg gta gca tac caa cta gtc aga gcc act gtg gtt tac cgc cat cag   1266
Arg Val Ala Tyr Gln Leu Val Arg Ala Thr Val Val Tyr Arg His Gln
100                 105                 110 ctt cac cta act cat tcc cac ctc tcc tgc cat gtg gag ccc tgg gtc   1314
Leu His Leu Thr His Ser His Leu Ser Cys His Val Glu Pro Trp Val
115                 120                 125                 130 cag aaa agc cca acc aat cac ttt cct tct tca gga aga ggc tcc tca   1362
Gln Lys Ser Pro Thr Asn His Phe Pro Ser Ser Gly Arg Gly Ser Ser
                135                 140                 145 aag cct tcc ctg ttg ccc aaa act tgg aca gag atg gat atc atg gaa   1410
Lys Pro Ser Leu Leu Pro Lys Thr Trp Thr Glu Met Asp Ile Met Glu
            150                 155                 160 cat gtt ggg caa aag ctc tgg aat cac aag ggg cgc agg gtt cta cga   1458
His Val Gly Gln Lys Leu Trp Asn His Lys Gly Arg Arg Val Leu Arg
        165                 170                 175 ctc cgc ttc gtg tgt cag cag cca aga ggt agt gag gtt ctt gag ttc   1506
Leu Arg Phe Val Cys Gln Gln Pro Arg Gly Ser Glu Val Leu Glu Phe
    180                 185                 190 tgg tgg cat ggc act tca tca ttg gac act gtc ttc ttg tta ctg tat   1554
Trp Trp His Gly Thr Ser Ser Leu Asp Thr Val Phe Leu Leu Leu Tyr
195                 200                 205                 210 ttc aat gac act cag agt gtt cag aag acc aaa cct ctc cct aaa ggc   1602
Phe Asn Asp Thr Gln Ser Val Gln Lys Thr Lys Pro Leu Pro Lys Gly
                215                 220                 225 ctg aaa gag ttt aca gaa aaa gac cct tct ctt ctc ttg agg agg gct   1650
Leu Lys Glu Phe Thr Glu Lys Asp Pro Ser Leu Leu Leu Arg Arg Ala
            230                 235                 240 cgt caa gca ggc agt att gca tcg gaa gtt cct ggc ccc tcc agg gag   1698
Arg Gln Ala Gly Ser Ile Ala Ser Glu Val Pro Gly Pro Ser Arg Glu
        245                 250                 255 cat gat ggg cct gaa agt aac cag tgt tcc ctc cac cct ttt caa gtc   1746
His Asp Gly Pro Glu Ser Asn Gln Cys Ser Leu His Pro Phe Gln Val
    260                 265                 270 agc ttc cag cag ctg ggc tgg gat cac tgg atc att gct ccc cat ctc   1794
Ser Phe Gln Gln Leu Gly Trp Asp His Trp Ile Ile Ala Pro His Leu
275                 280                 285                 290 tat acc cca aac tac tgt aag gga gta tgt cct cgg gta cta cac tat   1842
Tyr Thr Pro Asn Tyr Cys Lys Gly Val Cys Pro Arg Val Leu His Tyr
                295                 300                 305 ggt ctc aat tct ccc aat cat gcc atc atc cag aac ctt gtc agt gag   1890
Gly Leu Asn Ser Pro Asn His Ala Ile Ile Gln Asn Leu Val Ser Glu
            310                 315                 320 ctg gtg gat cag aat gtc cct cag cct tcc tgt gtc cct tat aag tat   1938
Leu Val Asp Gln Asn Val Pro Gln Pro Ser Cys Val Pro Tyr Lys Tyr
        325                 330                 335 gtt ccc att agc atc ctt ctg att gag gca aat ggg agt atc ttg tac   1986
Val Pro Ile Ser Ile Leu Leu Ile Glu Ala Asn Gly Ser Ile Leu Tyr
    340                 345                 350 aag gag tat gag ggt atg att gcc cag tcc tgc aca tgc agg          2028
Lys Glu Tyr Glu Gly Met Ile Ala Gln Ser Cys Thr Cys Arg
355                 360                 365 tgacggcaaa ggtgca                                                2044
```

<210> SEQ ID NO 2
<211> LENGTH: 393
<212> TYPE: PRT
<213> ORGANISM: Ovis aries
<220> FEATURE:
<221> NAME/KEY: SIGNAL
<222> LOCATION: (1)...(25)

<400> SEQUENCE: 2

```
Met Val Leu Leu Ser Ile Leu Arg Ile Leu Leu Trp Gly Leu Val Leu
-25                 -20                 -15                 -10

Phe Met Glu His Arg Val Gln Met Thr Gln Val Gly Gln Pro Ser Ile
            -5                   1                   5

Ala His Leu Pro Glu Ala Pro Thr Leu Pro Leu Ile Gln Glu Leu Leu
            10                  15                  20

Glu Glu Ala Pro Gly Lys Gln Gln Arg Lys Pro Arg Val Leu Gly His
            25                  30                  35

Pro Leu Arg Tyr Met Leu Glu Leu Tyr Gln Arg Ser Ala Asp Ala Ser
 40                  45                  50                  55

Gly His Pro Arg Glu Asn Arg Thr Ile Gly Ala Thr Met Val Arg Leu
                60                  65                  70

Val Arg Pro Leu Ala Ser Val Ala Arg Pro Leu Arg Gly Ser Trp His
                75                  80                  85

Ile Gln Thr Leu Asp Phe Pro Leu Arg Pro Asn Arg Val Ala Tyr Gln
                90                  95                 100

Leu Val Arg Ala Thr Val Val Tyr Arg His Gln Leu His Leu Thr His
               105                 110                 115

Ser His Leu Ser Cys His Val Glu Pro Trp Val Gln Lys Ser Pro Thr
120                 125                 130                 135

Asn His Phe Pro Ser Ser Gly Arg Gly Ser Ser Lys Pro Ser Leu Leu
                140                 145                 150

Pro Lys Thr Trp Thr Glu Met Asp Ile Met Glu His Val Gly Gln Lys
                155                 160                 165

Leu Trp Asn His Lys Gly Arg Arg Val Leu Arg Leu Arg Phe Val Cys
                170                 175                 180

Gln Gln Pro Arg Gly Ser Glu Val Leu Glu Phe Trp Trp His Gly Thr
185                 190                 195

Ser Ser Leu Asp Thr Val Phe Leu Leu Leu Tyr Phe Asn Asp Thr Gln
200                 205                 210                 215

Ser Val Gln Lys Thr Lys Pro Leu Pro Lys Gly Leu Lys Glu Phe Thr
                220                 225                 230

Glu Lys Asp Pro Ser Leu Leu Leu Arg Arg Ala Arg Gln Ala Gly Ser
                235                 240                 245

Ile Ala Ser Glu Val Pro Gly Pro Ser Arg Glu His Asp Gly Pro Glu
                250                 255                 260

Ser Asn Gln Cys Ser Leu His Pro Phe Gln Val Ser Phe Gln Gln Leu
                265                 270                 275

Gly Trp Asp His Trp Ile Ile Ala Pro His Leu Tyr Thr Pro Asn Tyr
280                 285                 290                 295

Cys Lys Gly Val Cys Pro Arg Val Leu His Tyr Gly Leu Asn Ser Pro
                300                 305                 310

Asn His Ala Ile Ile Gln Asn Leu Val Ser Glu Leu Val Asp Gln Asn
                315                 320                 325

Val Pro Gln Pro Ser Cys Val Pro Tyr Lys Tyr Val Pro Ile Ser Ile
                330                 335                 340
```

-continued

```
Leu Leu Ile Glu Ala Asn Gly Ser Ile Leu Tyr Lys Glu Tyr Glu Gly
    345                 350                 355

Met Ile Ala Gln Ser Cys Thr Cys Arg
360                 365

<210> SEQ ID NO 3
<211> LENGTH: 1195
<212> TYPE: DNA
<213> ORGANISM: Ovis aries
<220> FEATURE:
<221> NAME/KEY: CDS
<222> LOCATION: (1)...(1179)
<220> FEATURE:
<221> NAME/KEY: misc_feature
<222> LOCATION: (325)...(326)
<223> OTHER INFORMATION: position of intron in genomic sequence
<220> FEATURE:
<221> NAME/KEY: misc_feature
<222> LOCATION: (793)...(804)
<223> OTHER INFORMATION: furin protease cleavage sequence
<220> FEATURE:
<221> NAME/KEY: mat_peptide
<222> LOCATION: (805)...()
<220> FEATURE:
<221> NAME/KEY: misc_feature
<222> LOCATION: (896)...()
<223> OTHER INFORMATION: position of Inverdale mutation

<400> SEQUENCE: 3 atg gtc ctc ctg agc atc ctt aga atc ctt ctt tgg gga ctg gtg ctt      48
Met Val Leu Leu Ser Ile Leu Arg Ile Leu Leu Trp Gly Leu Val Leu
  1               5                  10                  15 ttt atg gaa cat agg gtc caa atg aca cag gta ggg cag ccc tct att      96
Phe Met Glu His Arg Val Gln Met Thr Gln Val Gly Gln Pro Ser Ile
             20                  25                  30 gcc cac ctg cct gag gcc cct acc ttg ccc ctg att cag gag ctg cta     144
Ala His Leu Pro Glu Ala Pro Thr Leu Pro Leu Ile Gln Glu Leu Leu
         35                  40                  45 gaa gaa gcc cct ggc aag cag cag agg aag ccg cgg gtc tta ggg cat     192
Glu Glu Ala Pro Gly Lys Gln Gln Arg Lys Pro Arg Val Leu Gly His
     50                  55                  60 ccc tta cgg tat atg ctg gag ctg tac cag cgt tca gct gac gca agt     240
Pro Leu Arg Tyr Met Leu Glu Leu Tyr Gln Arg Ser Ala Asp Ala Ser
 65                  70                  75                  80 gga cac cct agg gaa aac cgc acc att ggg gcc acc atg gtg agg ctg     288
Gly His Pro Arg Glu Asn Arg Thr Ile Gly Ala Thr Met Val Arg Leu
                 85                  90                  95 gtg agg ccg ctg gct agt gta gca agg cct ctc aga ggc tcc tgg cac     336
Val Arg Pro Leu Ala Ser Val Ala Arg Pro Leu Arg Gly Ser Trp His
            100                 105                 110 ata cag acc ctg gac ttt cct ctg aga cca aac cgg gta gca tac caa     384
Ile Gln Thr Leu Asp Phe Pro Leu Arg Pro Asn Arg Val Ala Tyr Gln
        115                 120                 125 cta gtc aga gcc act gtg gtt tac cgc cat cag ctt cac cta act cat     432
Leu Val Arg Ala Thr Val Val Tyr Arg His Gln Leu His Leu Thr His
    130                 135                 140 tcc cac ctc tcc tgc cat gtg gag ccc tgg gtc cag aaa agc cca acc     480
Ser His Leu Ser Cys His Val Glu Pro Trp Val Gln Lys Ser Pro Thr
145                 150                 155                 160 aat cac ttt cct tct tca gga aga ggc tcc tca aag cct tcc ctg ttg     528
Asn His Phe Pro Ser Ser Gly Arg Gly Ser Ser Lys Pro Ser Leu Leu
                165                 170                 175 ccc aaa act tgg aca gag atg gat atc atg gaa cat gtt ggg caa aag     576
Pro Lys Thr Trp Thr Glu Met Asp Ile Met Glu His Val Gly Gln Lys
```

-continued

```
                      180                 185                 190
ctc tgg aat cac aag ggg cgc agg gtt cta cga ctc cgc ttc gtg tgt    624
Leu Trp Asn His Lys Gly Arg Arg Val Leu Arg Leu Arg Phe Val Cys
            195                 200                 205 cag cag cca aga ggt agt gag gtt ctt gag ttc tgg tgg cat ggc act    672
Gln Gln Pro Arg Gly Ser Glu Val Leu Glu Phe Trp Trp His Gly Thr
        210                 215                 220 tca tca ttg gac act gtc ttc ttg tta ctg tat ttc aat gac act cag    720
Ser Ser Leu Asp Thr Val Phe Leu Leu Leu Tyr Phe Asn Asp Thr Gln
225                 230                 235                 240 agt gtt cag aag acc aaa cct ctc cct aaa ggc ctg aaa gag ttt aca    768
Ser Val Gln Lys Thr Lys Pro Leu Pro Lys Gly Leu Lys Glu Phe Thr
                245                 250                 255 gaa aaa gac cct tct ctt ctc ttg agg agg gct cgt caa gca ggc agt    816
Glu Lys Asp Pro Ser Leu Leu Leu Arg Arg Ala Arg Gln Ala Gly Ser
            260                 265                 270 att gca tcg gaa gtt cct ggc ccc tcc agg gag cat gat ggg cct gaa    864
Ile Ala Ser Glu Val Pro Gly Pro Ser Arg Glu His Asp Gly Pro Glu
        275                 280                 285 agt aac cag tgt tcc ctc cac cct ttt caa gac agc ttc cag cag ctg    912
Ser Asn Gln Cys Ser Leu His Pro Phe Gln Asp Ser Phe Gln Gln Leu
    290                 295                 300 ggc tgg gat cac tgg atc att gct ccc cat ctc tat acc cca aac tac    960
Gly Trp Asp His Trp Ile Ile Ala Pro His Leu Tyr Thr Pro Asn Tyr
305                 310                 315                 320 tgt aag gga gta tgt cct cgg gta cta cac tat ggt ctc aat tct ccc   1008
Cys Lys Gly Val Cys Pro Arg Val Leu His Tyr Gly Leu Asn Ser Pro
                325                 330                 335 aat cat gcc atc atc cag aac ctt gtc agt gag ctg gtg gat cag aat   1056
Asn His Ala Ile Ile Gln Asn Leu Val Ser Glu Leu Val Asp Gln Asn
            340                 345                 350 gtc cct cag cct tcc tgt gtc cct tat aag tat gtt ccc att agc atc   1104
Val Pro Gln Pro Ser Cys Val Pro Tyr Lys Tyr Val Pro Ile Ser Ile
        355                 360                 365 ctt ctg att gag gca aat ggg agt atc ttg tac aag gag tat gag ggt   1152
Leu Leu Ile Glu Ala Asn Gly Ser Ile Leu Tyr Lys Glu Tyr Glu Gly
    370                 375                 380 atg att gcc cag tcc tgc aca tgc agg tgacggcaaa ggtgca             1195
Met Ile Ala Gln Ser Cys Thr Cys Arg
385                 390
```

<210> SEQ ID NO 4
<211> LENGTH: 393
<212> TYPE: PRT
<213> ORGANISM: Ovis aries

<400> SEQUENCE: 4

```
Met Val Leu Leu Ser Ile Leu Arg Ile Leu Leu Trp Gly Leu Val Leu
  1               5                  10                  15

Phe Met Glu His Arg Val Gln Met Thr Gln Val Gly Gln Pro Ser Ile
                20                  25                  30

Ala His Leu Pro Glu Ala Pro Thr Leu Pro Leu Ile Gln Glu Leu Leu
            35                  40                  45

Glu Glu Ala Pro Gly Lys Gln Gln Arg Lys Pro Arg Val Leu Gly His
        50                  55                  60

Pro Leu Arg Tyr Met Leu Glu Leu Tyr Gln Arg Ser Ala Asp Ala Ser
 65                  70                  75                  80

Gly His Pro Arg Glu Asn Arg Thr Ile Gly Ala Thr Met Val Arg Leu
                85                  90                  95
```

```
Val Arg Pro Leu Ala Ser Val Ala Arg Pro Leu Arg Gly Ser Trp His
            100                 105                 110
Ile Gln Thr Leu Asp Phe Pro Leu Arg Pro Asn Arg Val Ala Tyr Gln
            115                 120                 125
Leu Val Arg Ala Thr Val Val Tyr Arg His Gln Leu His Leu Thr His
            130                 135                 140
Ser His Leu Ser Cys His Val Glu Pro Trp Val Gln Lys Ser Pro Thr
145                 150                 155                 160
Asn His Phe Pro Ser Ser Gly Arg Gly Ser Ser Lys Pro Ser Leu Leu
                    165                 170                 175
Pro Lys Thr Trp Thr Glu Met Asp Ile Met Glu His Val Gly Gln Lys
                180                 185                 190
Leu Trp Asn His Lys Gly Arg Arg Val Leu Arg Leu Arg Phe Val Cys
            195                 200                 205
Gln Gln Pro Arg Gly Ser Glu Val Leu Glu Phe Trp Trp His Gly Thr
            210                 215                 220
Ser Ser Leu Asp Thr Val Phe Leu Leu Leu Tyr Phe Asn Asp Thr Gln
225                 230                 235                 240
Ser Val Gln Lys Thr Lys Pro Leu Pro Lys Gly Leu Lys Glu Phe Thr
                    245                 250                 255
Glu Lys Asp Pro Ser Leu Leu Arg Arg Ala Arg Gln Ala Gly Ser
                260                 265                 270
Ile Ala Ser Glu Val Pro Gly Pro Ser Arg Glu His Asp Gly Pro Glu
            275                 280                 285
Ser Asn Gln Cys Ser Leu His Pro Phe Gln Asp Ser Phe Gln Gln Leu
290                 295                 300
Gly Trp Asp His Trp Ile Ile Ala Pro His Leu Tyr Thr Pro Asn Tyr
305                 310                 315                 320
Cys Lys Gly Val Cys Pro Arg Val Leu His Tyr Gly Leu Asn Ser Pro
                    325                 330                 335
Asn His Ala Ile Ile Gln Asn Leu Val Ser Glu Leu Val Asp Gln Asn
                340                 345                 350
Val Pro Gln Pro Ser Cys Val Pro Tyr Lys Tyr Val Pro Ile Ser Ile
            355                 360                 365
Leu Leu Ile Glu Ala Asn Gly Ser Ile Leu Tyr Lys Glu Tyr Glu Gly
            370                 375                 380
Met Ile Ala Gln Ser Cys Thr Cys Arg
385                 390

<210> SEQ ID NO 5
<211> LENGTH: 1195
<212> TYPE: DNA
<213> ORGANISM: Ovis Aries
<220> FEATURE:
<221> NAME/KEY: CDS
<222> LOCATION: (1)...(870)
<220> FEATURE:
<221> NAME/KEY: misc_feature
<222> LOCATION: (325)...(326)
<223> OTHER INFORMATION: position of intron in genomic sequence
<220> FEATURE:
<221> NAME/KEY: misc_feature
<222> LOCATION: (793)...(804)
<223> OTHER INFORMATION: furin protease cleavage sequence
<220> FEATURE:
<221> NAME/KEY: mat_peptide
<222> LOCATION: (805)...()
<220> FEATURE:
<221> NAME/KEY: misc_feature
```

-continued

```
<222> LOCATION: (871)...()
<223> OTHER INFORMATION: position of Hanna mutation

<400> SEQUENCE: 5 atg gtc ctc ctg agc atc ctt aga atc ctt ctt tgg gga ctg gtg ctt      48
Met Val Leu Leu Ser Ile Leu Arg Ile Leu Leu Trp Gly Leu Val Leu
 1               5                  10                  15 ttt atg gaa cat agg gtc caa atg aca cag gta ggg cag ccc tct att      96
Phe Met Glu His Arg Val Gln Met Thr Gln Val Gly Gln Pro Ser Ile
             20                  25                  30 gcc cac ctg cct gag gcc cct acc ttg ccc ctg att cag gag ctg cta     144
Ala His Leu Pro Glu Ala Pro Thr Leu Pro Leu Ile Gln Glu Leu Leu
         35                  40                  45 gaa gaa gcc cct ggc aag cag cag agg aag ccg cgg gtc tta ggg cat     192
Glu Glu Ala Pro Gly Lys Gln Gln Arg Lys Pro Arg Val Leu Gly His
     50                  55                  60 ccc tta cgg tat atg ctg gag ctg tac cag cgt tca gct gac gca agt     240
Pro Leu Arg Tyr Met Leu Glu Leu Tyr Gln Arg Ser Ala Asp Ala Ser
 65                  70                  75                  80 gga cac cct agg gaa aac cgc acc att ggg gcc acc atg gtg agg ctg     288
Gly His Pro Arg Glu Asn Arg Thr Ile Gly Ala Thr Met Val Arg Leu
                 85                  90                  95 gtg agg ccg ctg gct agt gta gca agg cct ctc aga ggc tcc tgg cac     336
Val Arg Pro Leu Ala Ser Val Ala Arg Pro Leu Arg Gly Ser Trp His
            100                 105                 110 ata cag acc ctg gac ttt cct ctg aga cca aac cgg gta gca tac caa     384
Ile Gln Thr Leu Asp Phe Pro Leu Arg Pro Asn Arg Val Ala Tyr Gln
        115                 120                 125 cta gtc aga gcc act gtg gtt tac cgc cat cag ctt cac cta act cat     432
Leu Val Arg Ala Thr Val Val Tyr Arg His Gln Leu His Leu Thr His
    130                 135                 140 tcc cac ctc tcc tgc cat gtg gag ccc tgg gtc cag aaa agc cca acc     480
Ser His Leu Ser Cys His Val Glu Pro Trp Val Gln Lys Ser Pro Thr
145                 150                 155                 160 aat cac ttt cct tct tca gga aga ggc tcc tca aag cct tcc ctg ttg     528
Asn His Phe Pro Ser Ser Gly Arg Gly Ser Ser Lys Pro Ser Leu Leu
                165                 170                 175 ccc aaa act tgg aca gag atg gat atc atg gaa cat gtt ggg caa aag     576
Pro Lys Thr Trp Thr Glu Met Asp Ile Met Glu His Val Gly Gln Lys
            180                 185                 190 ctc tgg aat cac aag ggg cgc agg gtt cta cga ctc cgc ttc gtg tgt     624
Leu Trp Asn His Lys Gly Arg Arg Val Leu Arg Leu Arg Phe Val Cys
        195                 200                 205 cag cag cca aga ggt agt gag gtt ctt gag ttc tgg tgg cat ggc act     672
Gln Gln Pro Arg Gly Ser Glu Val Leu Glu Phe Trp Trp His Gly Thr
    210                 215                 220 tca tca ttg gac act gtc ttc ttg tta ctg tat ttc aat gac act cag     720
Ser Ser Leu Asp Thr Val Phe Leu Leu Leu Tyr Phe Asn Asp Thr Gln
225                 230                 235                 240 agt gtt cag aag acc aaa cct ctc cct aaa ggc ctg aaa gag ttt aca     768
Ser Val Gln Lys Thr Lys Pro Leu Pro Lys Gly Leu Lys Glu Phe Thr
                245                 250                 255 gaa aaa gac cct tct ctt ctc ttg agg agg gct cgt caa gca ggc agt     816
Glu Lys Asp Pro Ser Leu Leu Leu Arg Arg Ala Arg Gln Ala Gly Ser
            260                 265                 270 att gca tcg gaa gtt cct ggc ccc tcc agg gag cat gat ggg cct gaa     864
Ile Ala Ser Glu Val Pro Gly Pro Ser Arg Glu His Asp Gly Pro Glu
        275                 280                 285 agt aac tagtgttccc tccacccttt tcaagtcagc ttcagcagc tgggctggga      920
Ser Asn
```

```
tcactggatc attgctcccc atctctatac cccaaactac tgtaagggag tatgtcctcg    980
ggtactacac tatggtctca attctcccaa tcatgccatc atccagaacc ttgtcagtga   1040
gctggtggat cagaatgtcc ctcagccttc ctgtgtccct tataagtatg ttcccattag   1100
catccttctg attgaggcaa atgggagtat cttgtacaag gagtatgagg gtatgattgc   1160
ccagtcctgc acatgcaggt gacggcaaag gtgca                              1195
```

<210> SEQ ID NO 6
<211> LENGTH: 290
<212> TYPE: PRT
<213> ORGANISM: Ovis Aries

<400> SEQUENCE: 6

```
Met Val Leu Leu Ser Ile Leu Arg Ile Leu Leu Trp Gly Leu Val Leu
 1               5                  10                  15

Phe Met Glu His Arg Val Gln Met Thr Gln Val Gly Gln Pro Ser Ile
            20                  25                  30

Ala His Leu Pro Glu Ala Pro Thr Leu Pro Leu Ile Gln Glu Leu Leu
        35                  40                  45

Glu Glu Ala Pro Gly Lys Gln Gln Arg Lys Pro Arg Val Leu Gly His
    50                  55                  60

Pro Leu Arg Tyr Met Leu Glu Leu Tyr Gln Arg Ser Ala Asp Ala Ser
65                  70                  75                  80

Gly His Pro Arg Glu Asn Arg Thr Ile Gly Ala Thr Met Val Arg Leu
                85                  90                  95

Val Arg Pro Leu Ala Ser Val Ala Arg Pro Leu Arg Gly Ser Trp His
            100                 105                 110

Ile Gln Thr Leu Asp Phe Pro Leu Arg Pro Asn Arg Val Ala Tyr Gln
        115                 120                 125

Leu Val Arg Ala Thr Val Val Tyr Arg His Gln Leu His Leu Thr His
    130                 135                 140

Ser His Leu Ser Cys His Val Glu Pro Trp Val Gln Lys Ser Pro Thr
145                 150                 155                 160

Asn His Phe Pro Ser Ser Gly Arg Gly Ser Ser Lys Pro Ser Leu Leu
                165                 170                 175

Pro Lys Thr Trp Thr Glu Met Asp Ile Met Glu His Val Gly Gln Lys
            180                 185                 190

Leu Trp Asn His Lys Gly Arg Arg Val Leu Arg Leu Arg Phe Val Cys
        195                 200                 205

Gln Gln Pro Arg Gly Ser Glu Val Leu Glu Phe Trp Trp His Gly Thr
    210                 215                 220

Ser Ser Leu Asp Thr Val Phe Leu Leu Leu Tyr Phe Asn Asp Thr Gln
225                 230                 235                 240

Ser Val Gln Lys Thr Lys Pro Leu Pro Lys Gly Leu Lys Glu Phe Thr
                245                 250                 255

Glu Lys Asp Pro Ser Leu Leu Leu Arg Arg Ala Arg Gln Ala Gly Ser
            260                 265                 270

Ile Ala Ser Glu Val Pro Gly Pro Ser Arg Glu His Asp Gly Pro Glu
        275                 280                 285

Ser Asn
    290
```

<210> SEQ ID NO 7

```
<211> LENGTH: 75
<212> TYPE: DNA
<213> ORGANISM: Ovis aries
<220> FEATURE:
<221> NAME/KEY: CDS
<222> LOCATION: (1)...(75)
<220> FEATURE:
<221> NAME/KEY: misc_feature
<222> LOCATION: (28)...(30)
<223> OTHER INFORMATION: ctt codon which is deleted in some sheep

<400> SEQUENCE: 7 atg gtc ctc ctg agc atc ctt aga atc ctt ctt tgg gga ctg gtg ctt      48
Met Val Leu Leu Ser Ile Leu Arg Ile Leu Leu Trp Gly Leu Val Leu
 1               5                  10                  15 ttt atg gaa cat agg gtc caa atg aca                                   75
Phe Met Glu His Arg Val Gln Met Thr
            20                  25

<210> SEQ ID NO 8
<211> LENGTH: 25
<212> TYPE: PRT
<213> ORGANISM: Ovis aries

<400> SEQUENCE: 8

Met Val Leu Leu Ser Ile Leu Arg Ile Leu Leu Trp Gly Leu Val Leu
 1               5                  10                  15

Phe Met Glu His Arg Val Gln Met Thr
            20                  25

<210> SEQ ID NO 9
<211> LENGTH: 72
<212> TYPE: DNA
<213> ORGANISM: Ovis Aries
<220> FEATURE:
<221> NAME/KEY: misc_feature
<222> LOCATION: (28)...(30)
<223> OTHER INFORMATION: probable atg start codon
<220> FEATURE:
<221> NAME/KEY: CDS
<222> LOCATION: (1)...(72)
<223> OTHER INFORMATION: cds if 3' atg is used
<220> FEATURE:
<221> NAME/KEY: misc_feature
<222> LOCATION: (1)...(72)
<223> OTHER INFORMATION: cds if 3' atg start codon is used

<400> SEQUENCE: 9 atg ttg ctg aac acc aag ctt ttc aag atg gtc ctc ctg agc atc ctt      48
Met Leu Leu Asn Thr Lys Leu Phe Lys Met Val Leu Leu Ser Ile Leu
 1               5                  10                  15 aga atc ctt ctt tgg gga ctg gtg                                       72
Arg Ile Leu Leu Trp Gly Leu Val
            20

<210> SEQ ID NO 10
<211> LENGTH: 24
<212> TYPE: PRT
<213> ORGANISM: Ovis Aries

<400> SEQUENCE: 10

Met Leu Leu Asn Thr Lys Leu Phe Lys Met Val Leu Leu Ser Ile Leu
 1               5                  10                  15

Arg Ile Leu Leu Trp Gly Leu Val
            20

<210> SEQ ID NO 11
```

```
<211> LENGTH: 759
<212> TYPE: DNA
<213> ORGANISM: Sus scrofa
<220> FEATURE:
<221> NAME/KEY: CDS
<222> LOCATION: (2)...(757)
<223> OTHER INFORMATION: sequence stops 5 nucleotides short of the stop
      codon
<220> FEATURE:
<221> NAME/KEY: mat_peptide
<222> LOCATION: (389)...()

<400> SEQUENCE: 11 a ctt cac cta gct ccc ttc cac ctc tcc tgc cat gtg gag ccc tgg atc      49
  Leu His Leu Ala Pro Phe His Leu Ser Cys His Val Glu Pro Trp Ile
   1               5                  10                  15 cag aaa agc aca acc agt cac ttt cct tcc tca gga aga ggc tcc tta       97
Gln Lys Ser Thr Thr Ser His Phe Pro Ser Ser Gly Arg Gly Ser Leu
           20                  25                  30 aag cct tcc ctg ctg ccc caa gct tgg acg gag atg gat gtc acg caa      145
Lys Pro Ser Leu Leu Pro Gln Ala Trp Thr Glu Met Asp Val Thr Gln
        35                  40                  45 cat gtt gga caa aag ctc tgg aat cac aag ggg cgc agg gtt cta cga      193
His Val Gly Gln Lys Leu Trp Asn His Lys Gly Arg Arg Val Leu Arg
 50                  55                  60 ctc cgc ttc atg tgt cag cag caa aat ggt agt gag att ctt gag ttc      241
Leu Arg Phe Met Cys Gln Gln Gln Asn Gly Ser Glu Ile Leu Glu Phe
 65                  70                  75                  80 cgg ggg cgt ggc att tca tcc ctg gac act gcc ttc ttg tta ctc tat      289
Arg Gly Arg Gly Ile Ser Ser Leu Asp Thr Ala Phe Leu Leu Leu Tyr
                 85                  90                  95 ttc aat gac act cgg agt gtt cag aag gcc aaa ctt ctt ccc aga ggc      337
Phe Asn Asp Thr Arg Ser Val Gln Lys Ala Lys Leu Leu Pro Arg Gly
             100                 105                 110 ctg gaa gag ttt atg gca aga gac cct tct ctt ctt ttg cgg aag gcc      385
Leu Glu Glu Phe Met Ala Arg Asp Pro Ser Leu Leu Leu Arg Lys Ala
        115                 120                 125 cgg caa gca ggc agc atc gca tct gag gtt ctt ggc ccc tcc agg gag      433
Arg Gln Ala Gly Ser Ile Ala Ser Glu Val Leu Gly Pro Ser Arg Glu
130                 135                 140 cac gat ggg cct gaa agt aac cag tgt tcc ctc cat cct ttc caa gtc      481
His Asp Gly Pro Glu Ser Asn Gln Cys Ser Leu His Pro Phe Gln Val
145                 150                 155                 160 agc ttc cac caa ctg ggt tgg gat cat tgg atc att gct ccc cat ttc      529
Ser Phe His Gln Leu Gly Trp Asp His Trp Ile Ile Ala Pro His Phe
                165                 170                 175 tat acc cca aac tac tgt aag ggg gtc tgc cct cgg gta cta cac tat      577
Tyr Thr Pro Asn Tyr Cys Lys Gly Val Cys Pro Arg Val Leu His Tyr
            180                 185                 190 ggt ctc aat tcc ccc aat cat gcc atc atc cag aac ctt gtc aat gag      625
Gly Leu Asn Ser Pro Asn His Ala Ile Ile Gln Asn Leu Val Asn Glu
        195                 200                 205 ctg gtg gac cag agt gtc cct cag ccc tcc tgt gtc cct tat aag tat      673
Leu Val Asp Gln Ser Val Pro Gln Pro Ser Cys Val Pro Tyr Lys Tyr
    210                 215                 220 gtg cct att agc atc ctc ctg att gag gca aat ggg agt atc ttg tac      721
Val Pro Ile Ser Ile Leu Leu Ile Glu Ala Asn Gly Ser Ile Leu Tyr
225                 230                 235                 240 aag gag tat gag gat atg att gcc cag tcc tgt acg tg                    759
Lys Glu Tyr Glu Asp Met Ile Ala Gln Ser Cys Thr
                245                 250
```

-continued

```
<210> SEQ ID NO 12
<211> LENGTH: 252
<212> TYPE: PRT
<213> ORGANISM: Sus scrofa

<400> SEQUENCE: 12

Leu His Leu Ala Pro Phe His Leu Ser Cys His Val Glu Pro Trp Ile
1               5                   10                  15

Gln Lys Ser Thr Thr Ser His Phe Pro Ser Ser Gly Arg Gly Ser Leu
            20                  25                  30

Lys Pro Ser Leu Leu Pro Gln Ala Trp Thr Glu Met Asp Val Thr Gln
        35                  40                  45

His Val Gly Gln Lys Leu Trp Asn His Lys Gly Arg Arg Val Leu Arg
    50                  55                  60

Leu Arg Phe Met Cys Gln Gln Gln Asn Gly Ser Glu Ile Leu Glu Phe
65                  70                  75                  80

Arg Gly Arg Gly Ile Ser Ser Leu Asp Thr Ala Phe Leu Leu Leu Tyr
                85                  90                  95

Phe Asn Asp Thr Arg Ser Val Gln Lys Ala Lys Leu Leu Pro Arg Gly
            100                 105                 110

Leu Glu Glu Phe Met Ala Arg Asp Pro Ser Leu Leu Leu Arg Lys Ala
        115                 120                 125

Arg Gln Ala Gly Ser Ile Ala Ser Glu Val Leu Gly Pro Ser Arg Glu
    130                 135                 140

His Asp Gly Pro Glu Ser Asn Gln Cys Ser Leu His Pro Phe Gln Val
145                 150                 155                 160

Ser Phe His Gln Leu Gly Trp Asp His Trp Ile Ile Ala Pro His Phe
                165                 170                 175

Tyr Thr Pro Asn Tyr Cys Lys Gly Val Cys Pro Arg Val Leu His Tyr
            180                 185                 190

Gly Leu Asn Ser Pro Asn His Ala Ile Ile Gln Asn Leu Val Asn Glu
        195                 200                 205

Leu Val Asp Gln Ser Val Pro Gln Pro Ser Cys Val Pro Tyr Lys Tyr
    210                 215                 220

Val Pro Ile Ser Ile Leu Leu Ile Glu Ala Asn Gly Ser Ile Leu Tyr
225                 230                 235                 240

Lys Glu Tyr Glu Asp Met Ile Ala Gln Ser Cys Thr
                245                 250

<210> SEQ ID NO 13
<211> LENGTH: 857
<212> TYPE: DNA
<213> ORGANISM: Cervus elaphus
<220> FEATURE:
<221> NAME/KEY: CDS
<222> LOCATION: (3)...(854)
<220> FEATURE:
<221> NAME/KEY: mat_peptide
<222> LOCATION: (480)...()

<400> SEQUENCE: 13 gc tcc tgg cac ata cag acc ctg gac ttt cct ctg aga cca aac cgg      47
   Ser Trp His Ile Gln Thr Leu Asp Phe Pro Leu Arg Pro Asn Arg
   1               5                   10                  15 gta gcc tac caa cta gtc aga gcc act gtg gtt tac cgc cat caa ctt     95
Val Ala Tyr Gln Leu Val Arg Ala Thr Val Val Tyr Arg His Gln Leu
            20                  25                  30 cac cta act cat tcc cac ctc tcc tgc cat gtg gag ccc tgg atc cag    143
His Leu Thr His Ser His Leu Ser Cys His Val Glu Pro Trp Ile Gln
```

```
                   35                  40                  45
aaa agc cca acc agt cac ttt cct tct tca gga aga ggc tcc tca aag       191
Lys Ser Pro Thr Ser His Phe Pro Ser Ser Gly Arg Gly Ser Ser Lys
            50                  55                  60 cct tcc ctg ctg ccc aaa gct tgg aca gag atg gat atc atg gaa cat       239
Pro Ser Leu Leu Pro Lys Ala Trp Thr Glu Met Asp Ile Met Glu His
65                  70                  75 gtt gga caa aag ctg tgg aat cgc aag ggg cgc agg gtt cta cga ctc       287
Val Gly Gln Lys Leu Trp Asn Arg Lys Gly Arg Arg Val Leu Arg Leu
80                  85                  90                  95 cgc ttc atg tgt cag cag cca aga ggt agt gag gtt ctt gag ttc tgg       335
Arg Phe Met Cys Gln Gln Pro Arg Gly Ser Glu Val Leu Glu Phe Trp
                100                 105                 110 tgg cat ggc act tca tca ttg gac act gtc ttc ttg tta ctg tat ttc       383
Trp His Gly Thr Ser Ser Leu Asp Thr Val Phe Leu Leu Leu Tyr Phe
            115                 120                 125 aat gac act cag agt gtt cag aag acc aaa cct ctc cct aaa ggc ctg       431
Asn Asp Thr Gln Ser Val Gln Lys Thr Lys Pro Leu Pro Lys Gly Leu
        130                 135                 140 aaa gag ttt aca gaa aaa gac cct tct ctt ctc ttg agg agg gct cgt       479
Lys Glu Phe Thr Glu Lys Asp Pro Ser Leu Leu Leu Arg Arg Ala Arg
145                 150                 155 caa gca ggc agt atc gca tct gaa gtt cct ggc ccc tcc agg gag cat       527
Gln Ala Gly Ser Ile Ala Ser Glu Val Pro Gly Pro Ser Arg Glu His
160                 165                 170                 175 gat ggg cct gaa agt aac cag tgt tcc ctc cac cct ttt caa gtc agc       575
Asp Gly Pro Glu Ser Asn Gln Cys Ser Leu His Pro Phe Gln Val Ser
                180                 185                 190 ttc cag cag ctg ggc tgg gat cac tgg atc att gct ccc aat ctc tat       623
Phe Gln Gln Leu Gly Trp Asp His Trp Ile Ile Ala Pro Asn Leu Tyr
            195                 200                 205 acc cca aac tac tgt aag gga gtg tgt cct cgg gta cta cac tat ggt       671
Thr Pro Asn Tyr Cys Lys Gly Val Cys Pro Arg Val Leu His Tyr Gly
        210                 215                 220 ctc aat tct ccc aat cat gcc atc atc cag aac ctt gtc aat gag ctg       719
Leu Asn Ser Pro Asn His Ala Ile Ile Gln Asn Leu Val Asn Glu Leu
225                 230                 235 gtg gat cag agt gtc cct cag cct tcc tgt gtc cct tat aag tat gtt       767
Val Asp Gln Ser Val Pro Gln Pro Ser Cys Val Pro Tyr Lys Tyr Val
240                 245                 250                 255 ccc att agc atc ctg ctg att gag gca aat ggg agt atc ttg tac aag       815
Pro Ile Ser Ile Leu Leu Ile Glu Ala Asn Gly Ser Ile Leu Tyr Lys
                260                 265                 270 gag tat gag ggt atg att gcc cag tcc tgc aca tgc agg tga              857
Glu Tyr Glu Gly Met Ile Ala Gln Ser Cys Thr Cys Arg
            275                 280

<210> SEQ ID NO 14
<211> LENGTH: 284
<212> TYPE: PRT
<213> ORGANISM: Cervus elaphus

<400> SEQUENCE: 14

Ser Trp His Ile Gln Thr Leu Asp Phe Pro Leu Arg Pro Asn Arg Val
1               5                   10                  15

Ala Tyr Gln Leu Val Arg Ala Thr Val Val Tyr Arg His Gln Leu His
                20                  25                  30

Leu Thr His Ser His Leu Ser Cys His Val Glu Pro Trp Ile Gln Lys
        35                  40                  45
```

```
Ser Pro Thr Ser His Phe Pro Ser Ser Gly Arg Gly Ser Lys Pro
 50                  55                  60

Ser Leu Leu Pro Lys Ala Trp Thr Glu Met Asp Ile Met Glu His Val
 65                  70                  75                  80

Gly Gln Lys Leu Trp Asn Arg Lys Gly Arg Val Leu Arg Leu Arg
                 85                  90                  95

Phe Met Cys Gln Gln Pro Arg Gly Ser Glu Val Leu Glu Phe Trp Trp
             100                 105                 110

His Gly Thr Ser Ser Leu Asp Thr Val Phe Leu Leu Tyr Phe Asn
             115                 120                 125

Asp Thr Gln Ser Val Gln Lys Thr Lys Pro Leu Pro Lys Gly Leu Lys
    130                 135                 140

Glu Phe Thr Glu Lys Asp Pro Ser Leu Leu Arg Arg Ala Arg Gln
145                 150                 155                 160

Ala Gly Ser Ile Ala Ser Glu Val Pro Gly Pro Ser Arg Glu His Asp
                165                 170                 175

Gly Pro Glu Ser Asn Gln Cys Ser Leu His Pro Phe Gln Val Ser Phe
            180                 185                 190

Gln Gln Leu Gly Trp Asp His Trp Ile Ile Ala Pro Asn Leu Tyr Thr
            195                 200                 205

Pro Asn Tyr Cys Lys Gly Val Cys Pro Arg Val Leu His Tyr Gly Leu
210                 215                 220

Asn Ser Pro Asn His Ala Ile Ile Gln Asn Leu Val Asn Glu Leu Val
225                 230                 235                 240

Asp Gln Ser Val Pro Gln Pro Ser Cys Val Pro Tyr Lys Tyr Val Pro
                245                 250                 255

Ile Ser Ile Leu Leu Ile Glu Ala Asn Gly Ser Ile Leu Tyr Lys Glu
            260                 265                 270

Tyr Glu Gly Met Ile Ala Gln Ser Cys Thr Cys Arg
            275                 280

<210> SEQ ID NO 15
<211> LENGTH: 857
<212> TYPE: DNA
<213> ORGANISM: Capra hircus
<220> FEATURE:
<221> NAME/KEY: CDS
<222> LOCATION: (3)...(854)
<220> FEATURE:
<221> NAME/KEY: mat_peptide
<222> LOCATION: (480)...()

<400> SEQUENCE: 15 gc tcc tgg cac ata cag acc ctg gac ttt cct ctg aga cca aac cgg      47
   Ser Trp His Ile Gln Thr Leu Asp Phe Pro Leu Arg Pro Asn Arg
    1               5                  10                  15 gta gca tac caa cta gtc aga gcc act gtg gtt tac cgc cat cag ctt     95
Val Ala Tyr Gln Leu Val Arg Ala Thr Val Val Tyr Arg His Gln Leu
             20                  25                  30 cac cta act cat tcc cac ctc tcc tgc cat gtg gag ccc tgg ggg cag    143
His Leu Thr His Ser His Leu Ser Cys His Val Glu Pro Trp Gly Gln
         35                  40                  45 aaa agc cca acc aat cac ttt cct tct tca gga aga ggc tcc cca aag    191
Lys Ser Pro Thr Asn His Phe Pro Ser Ser Gly Arg Gly Ser Pro Lys
     50                  55                  60 cct tcc ctg ttg ccc aaa act tgg aca gag atg gat atc atg gaa cat    239
Pro Ser Leu Leu Pro Lys Thr Trp Thr Glu Met Asp Ile Met Glu His
 65                  70                  75
```

```
gtt ggg caa aag ctc tgg aat cac aag ggg cgc agg gtt cta cga ctc       287
Val Gly Gln Lys Leu Trp Asn His Lys Gly Arg Arg Val Leu Arg Leu
 80                  85                  90                  95 cgc ttc gta tgt cag cag cca aga ggt agt gag gtt ctt gag ttc tgg       335
Arg Phe Val Cys Gln Gln Pro Arg Gly Ser Glu Val Leu Glu Phe Trp
            100                 105                 110 tgg cat ggc act tca tca ttg gac act gtc ttc ttg tta ctg tat ttc       383
Trp His Gly Thr Ser Ser Leu Asp Thr Val Phe Leu Leu Leu Tyr Phe
            115                 120                 125 aat gac act cag agt gtt cag aaa acc aaa cct ctc cct aaa ggc ctg       431
Asn Asp Thr Gln Ser Val Gln Lys Thr Lys Pro Leu Pro Lys Gly Leu
            130                 135                 140 aaa gag ttt aca gaa aaa gac cct tct ctt ctc ttg agg agg gct cgt       479
Lys Glu Phe Thr Glu Lys Asp Pro Ser Leu Leu Leu Arg Arg Ala Arg
145                 150                 155 caa gca ggc agt att gca tct gaa gtt cct ggc ccc tcc agg gag cat       527
Gln Ala Gly Ser Ile Ala Ser Glu Val Pro Gly Pro Ser Arg Glu His
160                 165                 170                 175 gat ggg cct gaa agt aac cag tgt tcc ctc cac cct ttt caa gtc agc       575
Asp Gly Pro Glu Ser Asn Gln Cys Ser Leu His Pro Phe Gln Val Ser
                180                 185                 190 ttc cag cag ctg ggc tgg gat cac tgg atc att gct ccc cat ctc tat       623
Phe Gln Gln Leu Gly Trp Asp His Trp Ile Ile Ala Pro His Leu Tyr
                195                 200                 205 acc cca aac tac tgt aag gga gta tgt cct cgg gta cta tac tat ggt       671
Thr Pro Asn Tyr Cys Lys Gly Val Cys Pro Arg Val Leu Tyr Tyr Gly
                210                 215                 220 ctc aat tct ccc aat cat gcc atc atc cag aac ctt gtc aat gag ctg       719
Leu Asn Ser Pro Asn His Ala Ile Ile Gln Asn Leu Val Asn Glu Leu
            225                 230                 235 gtg gat cag aat gtc cct cag cct tcc tgt gtc cct tat aag tat gtt       767
Val Asp Gln Asn Val Pro Gln Pro Ser Cys Val Pro Tyr Lys Tyr Val
240                 245                 250                 255 ccc att agc atc ctt ctg att gag gca aat ggg agt atc ttg tac aag       815
Pro Ile Ser Ile Leu Leu Ile Glu Ala Asn Gly Ser Ile Leu Tyr Lys
                260                 265                 270 gag tat gag ggt atg att gcc cag tcc tgc aca tgc agg tga               857
Glu Tyr Glu Gly Met Ile Ala Gln Ser Cys Thr Cys Arg
            275                 280
```

<210> SEQ ID NO 16
<211> LENGTH: 284
<212> TYPE: PRT
<213> ORGANISM: Capra hircus

<400> SEQUENCE: 16

```
Ser Trp His Ile Gln Thr Leu Asp Phe Pro Leu Arg Pro Asn Arg Val
 1               5                   10                  15

Ala Tyr Gln Leu Val Arg Ala Thr Val Val Tyr Arg His Gln Leu His
            20                  25                  30

Leu Thr His Ser His Leu Ser Cys His Val Glu Pro Trp Gly Gln Lys
        35                  40                  45

Ser Pro Thr Asn His Phe Pro Ser Ser Gly Arg Gly Ser Pro Lys Pro
    50                  55                  60

Ser Leu Leu Pro Lys Thr Trp Thr Glu Met Asp Ile Met Glu His Val
65                  70                  75                  80

Gly Gln Lys Leu Trp Asn His Lys Gly Arg Arg Val Leu Arg Leu Arg
                85                  90                  95

Phe Val Cys Gln Gln Pro Arg Gly Ser Glu Val Leu Glu Phe Trp Trp
```

```
                    100                 105                 110
His Gly Thr Ser Ser Leu Asp Thr Val Phe Leu Leu Tyr Phe Asn
        115                 120                 125
Asp Thr Gln Ser Val Gln Lys Thr Lys Pro Leu Pro Lys Gly Leu Lys
    130                 135                 140
Glu Phe Thr Glu Lys Asp Pro Ser Leu Leu Arg Ala Arg Gln
145                 150                 155                 160
Ala Gly Ser Ile Ala Ser Glu Val Pro Gly Pro Ser Arg Glu His Asp
                165                 170                 175
Gly Pro Glu Ser Asn Gln Cys Ser Leu His Pro Phe Gln Val Ser Phe
            180                 185                 190
Gln Gln Leu Gly Trp Asp His Trp Ile Ile Ala Pro His Leu Tyr Thr
        195                 200                 205
Pro Asn Tyr Cys Lys Gly Val Cys Pro Arg Val Leu Tyr Tyr Gly Leu
    210                 215                 220
Asn Ser Pro Asn His Ala Ile Ile Gln Asn Leu Val Asn Glu Leu Val
225                 230                 235                 240
Asp Gln Asn Val Pro Gln Pro Ser Cys Val Pro Tyr Lys Tyr Val Pro
                245                 250                 255
Ile Ser Ile Leu Leu Ile Glu Ala Asn Gly Ser Ile Leu Tyr Lys Glu
            260                 265                 270
Tyr Glu Gly Met Ile Ala Gln Ser Cys Thr Cys Arg
        275                 280

<210> SEQ ID NO 17
<211> LENGTH: 16
<212> TYPE: PRT
<213> ORGANISM: Ovis aries

<400> SEQUENCE: 17

Ser Glu Val Pro Gly Pro Ser Arg Glu His Asp Gly Pro Glu Ser Cys
1               5                   10                  15

<210> SEQ ID NO 18
<211> LENGTH: 16
<212> TYPE: PRT
<213> ORGANISM: Ovis aries

<400> SEQUENCE: 18

Lys Lys Pro Leu Val Pro Ala Ser Val Asn Leu Ser Glu Tyr Phe Cys
1               5                   10                  15

<210> SEQ ID NO 19
<211> LENGTH: 250
<212> TYPE: DNA
<213> ORGANISM: Ovis aries

<400> SEQUENCE: 19
acccttctct tctcttgagg agggctcgtc aagcaggcag tattgcatcg gaagttcctg      60
gcccctccag ggagcatgat gggcctgaaa gtaaccagtg ttccctccac ccttttcaag     120
acagcttcca gcagctgggc tgggatcact ggatcattgc tccccatctc tatacccaa     180 actactgtaa gggagtatgt cctcgggtac tacactatgg tctcaattct cccaatcatg     240
ccatcatcca                                                           250

<210> SEQ ID NO 20
<211> LENGTH: 300
<212> TYPE: DNA
```

```
-continued

<213> ORGANISM: Ovis aries

<400> SEQUENCE: 20
tcagaagacc aaacctctcc ctaaaggcct gaaagagttt acagaaaaag acccttctct        60
tctcttgagg agggctctgc aagcaggcag tattgcatcg gaagttcctg gcccctccag       120
ggagcatgat gggcctgaaa gtaactagtg ttccctccac ccttttcaag tcagcttcca       180
gcagctgggc tgggatcact ggatcattgc tccccatctc tatacccaa actactgtaa       240 gggagtatgt cctcgggtac tacactatgg tctcaattct cccaatcatg ccatcatcca      300
```